(12) United States Patent
Richardson

(10) Patent No.: US 10,993,853 B2
(45) Date of Patent: May 4, 2021

(54) DETACHABLE DISPOSABLE ABSORBENT ARTICLE

(71) Applicant: Irene Richardson, Newnan, GA (US)

(72) Inventor: Irene Richardson, Newnan, GA (US)

(*) Notice: Subject to any disclaimer, the term of this patent is extended or adjusted under 35 U.S.C. 154(b) by 300 days.

(21) Appl. No.: 16/033,210

(22) Filed: Jul. 12, 2018

(65) Prior Publication Data

US 2018/0338871 A1 Nov. 29, 2018

Related U.S. Application Data

(62) Division of application No. 15/458,005, filed on Mar. 13, 2017, now Pat. No. 10,052,241.

(51) Int. Cl.
   *A61F 13/505* (2006.01)
   *A61F 13/15* (2006.01)
   *A61F 13/84* (2006.01)

(52) U.S. Cl.
   CPC ...... *A61F 13/505* (2013.01); *A61F 13/15252* (2013.01); *A61F 13/84* (2013.01); *A61F 2013/8402* (2013.01)

(58) Field of Classification Search
   CPC ........ A61F 13/15252; A61F 2013/1526; A61F 13/515; A61F 2013/51447; A61F 13/51458; A61F 13/511; A61F 13/505; A61F 13/84; A61F 2013/8402
   See application file for complete search history.

(56) References Cited

U.S. PATENT DOCUMENTS

| | | | | |
|---|---|---|---|---|
| 5,026,363 A | * | 6/1991 | Pratt | A61F 13/15211 604/366 |
| 5,405,342 A | * | 4/1995 | Roessler | A61F 13/15211 604/364 |
| 5,830,201 A | * | 11/1998 | George | A61F 13/15252 604/364 |
| 6,623,466 B1 | * | 9/2003 | Richardson | A61F 13/15211 604/385.11 |
| 6,929,628 B2 | * | 8/2005 | George | A61F 13/15211 604/385.11 |
| 2017/0216111 A1 | * | 8/2017 | Kleuskens | A61F 13/5616 |

FOREIGN PATENT DOCUMENTS

| | | | | |
|---|---|---|---|---|
| DE | 102011007821 A1 | * | 10/2012 | A61F 13/70 |
| EP | 0549988 A1 | * | 7/1993 | A61F 13/15211 |
| WO | WO-9415563 A1 | * | 7/1994 | A61F 13/15211 |

* cited by examiner

*Primary Examiner* — Amy R Weisberg

(57) ABSTRACT

A disposable absorbent article utilized for absorption and containment of urine and other body exudates may incorporate components that may be detached from the article after use to provide disposal options based upon the user's preferences and circumstances, such as flushing down a toilet or septic tank, composting, recycling, or disposing in a landfill. Sanitary grips and sanitary gap may provide sanitary placements to detach the article. Ripping features incorporated along the top liner, back liner, or outer liner enclosure may also be used to detach the article. A removable liner may be detached from the top liner or outer liner enclosure. The absorbent core may be released after the article has been detached. To reduce the risk of clogging the toilet, a membrane may be utilized to create a barrier between the absorbent core and high-absorbency material to obstruct the high-absorbency material from being released and flushed.

20 Claims, 19 Drawing Sheets

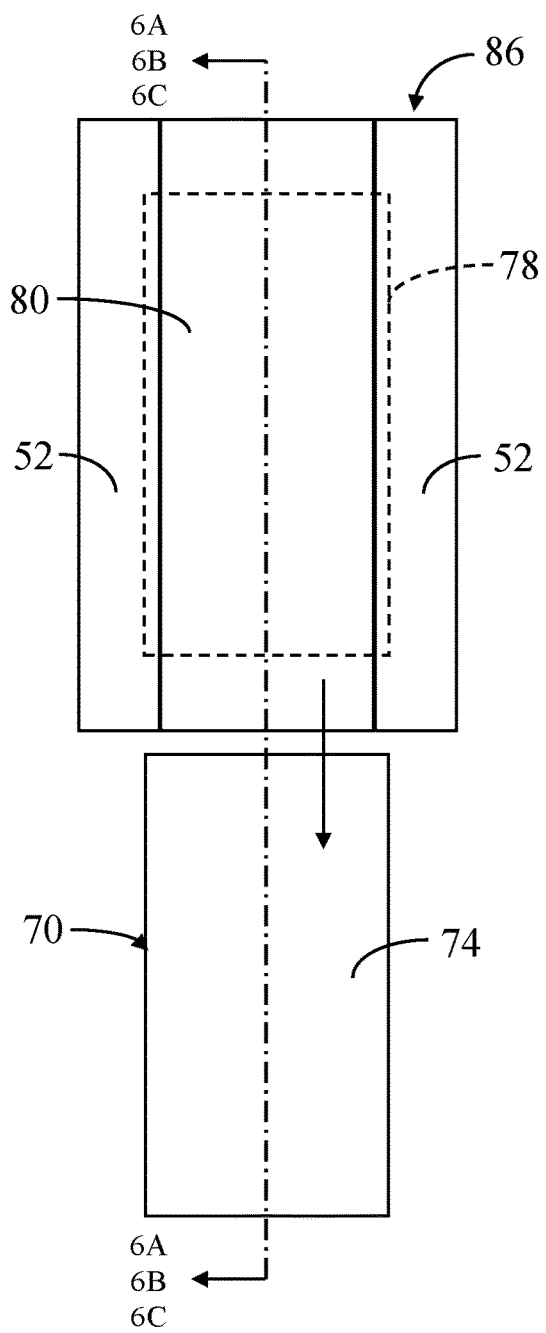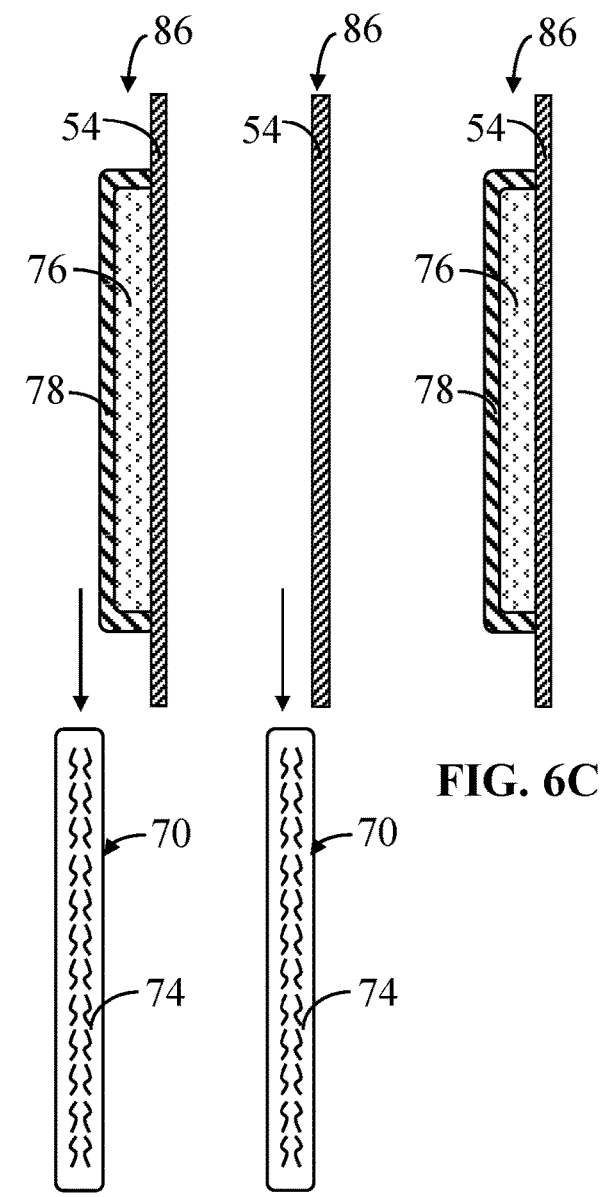
FIG. 6A  FIG. 6B  FIG. 6C
FIG. 6

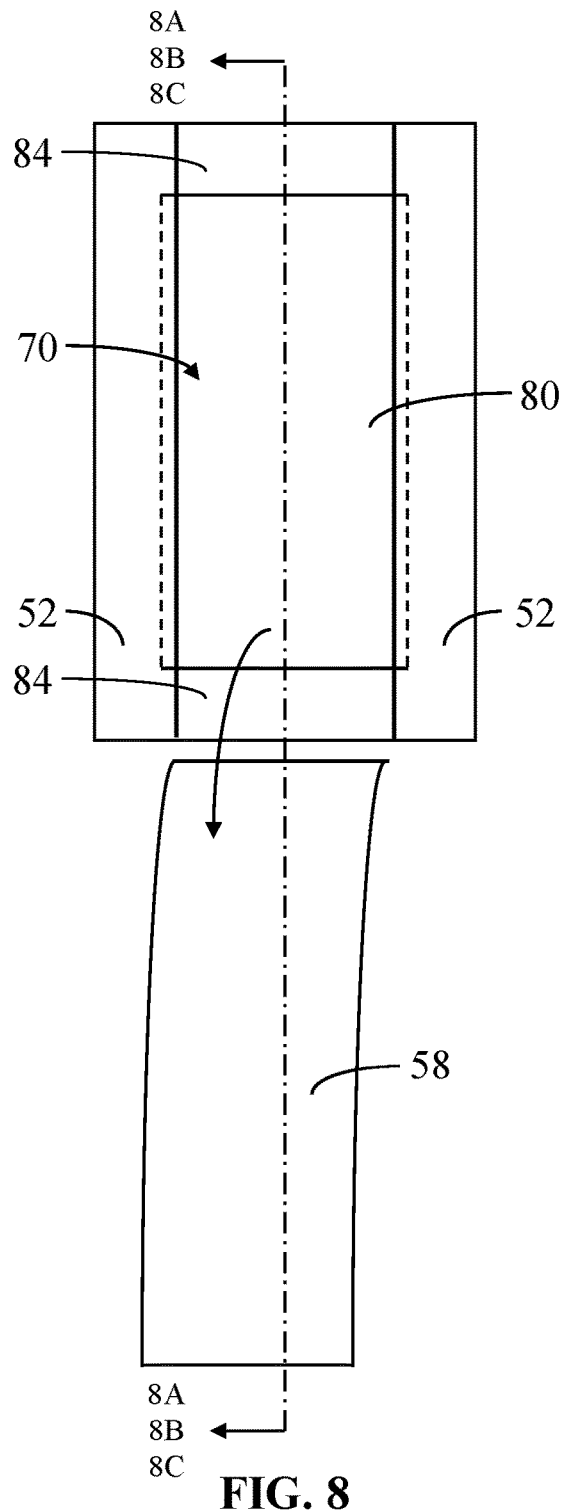 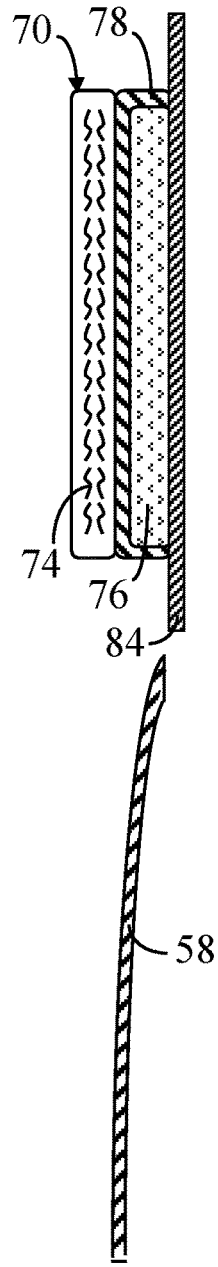 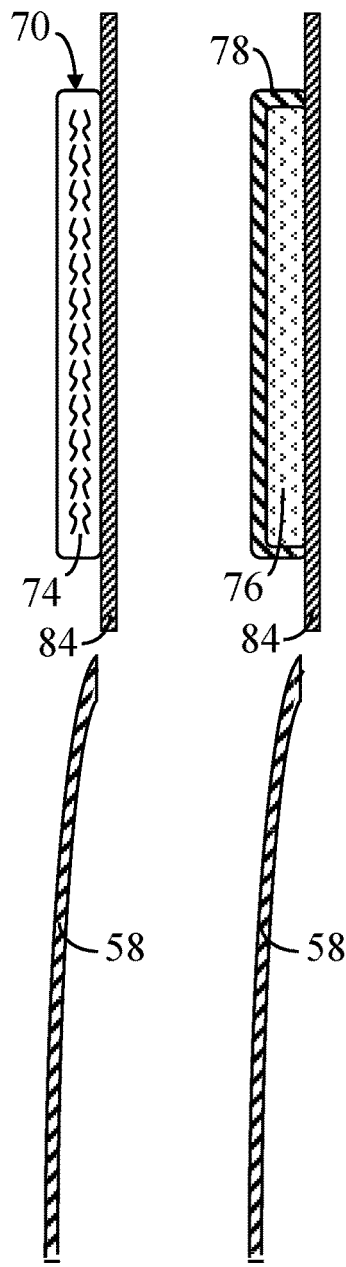
FIG. 8  FIG. 8A  FIG. 8B  FIG. 8C

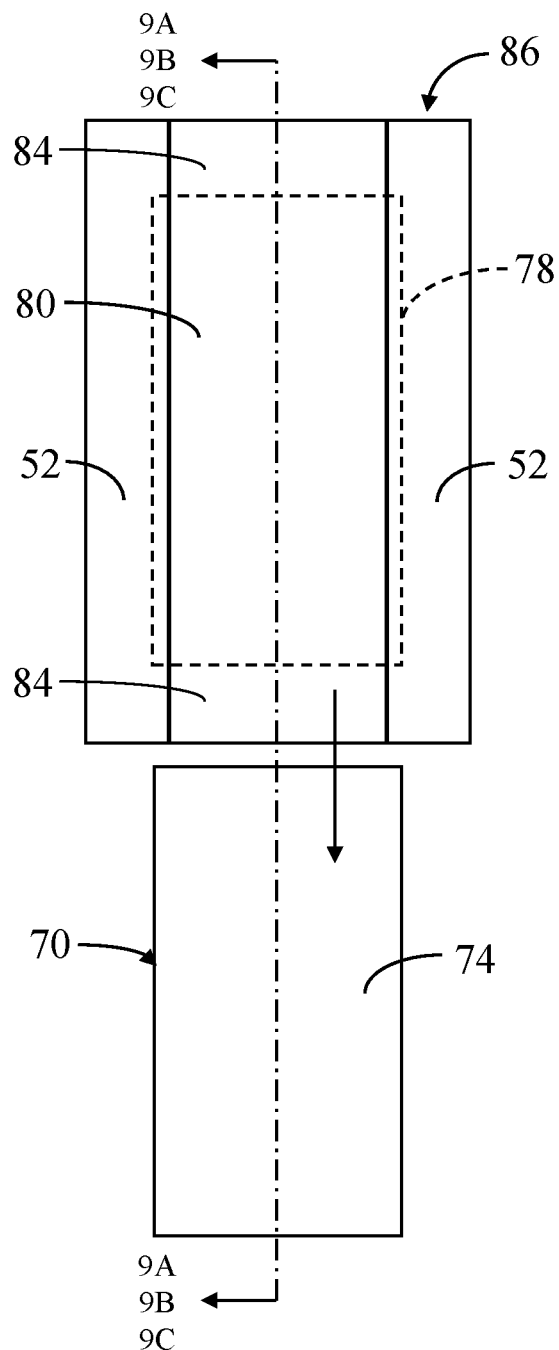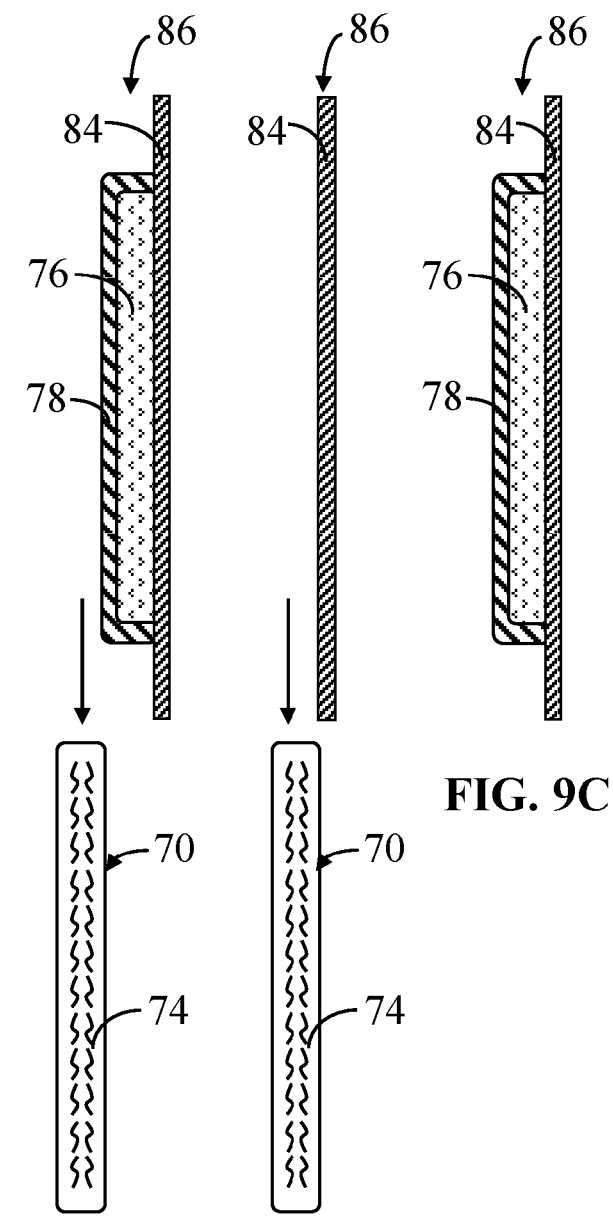
FIG. 9C
FIG. 9A   FIG. 9B
FIG. 9

DETACHABLE DISPOSABLE ABSORBENT ARTICLE

CROSS-REFERENCE TO RELATED APPLICATION

This is a divisional application of U.S. Nonprovisional patent application Ser. No. 15/458,005 filed on Mar. 13, 2017, the entire content of which is hereby incorporated herein by reference. This application claims the benefit of the filing date of U.S. Provisional Patent Application No. 62/309,888 filed on Mar. 17, 2016 by the present inventor.

FIELD

The present disclosure relates generally to the field of disposable absorbent articles utilized for the absorption and containment of urine and other body exudates, such as disposable diapers, disposable training pants, disposable inserts, disposable absorbent pads, disposable incontinence articles, feminine care pads, and the like. More particularly, the disclosure relates to a disposable absorbent article that incorporates components that may be detached from the article after use to provide disposal options for each of the detached components.

BACKGROUND

Disposable articles for the absorption and containment of urine and other body exudates are generally known in the art. Such disposable articles have found particular utility in the fields of infant care, child care, feminine care, and adult incontinency. Present commercially available disposable articles for such uses are generally unitary and are comprised of a liquid permeable top liner, a liquid impermeable backsheet, and an absorbent core disposed between the top liner and the backsheet. Disposable articles of this type effectively and efficiently absorb and contain urine or other body exudates. Such articles are designed for a single use and are simply discarded after use in a waste receptacle prior to being transported to a landfill. This ease and convenience of disposal has contributed to the increasing popularity of such disposable absorbent articles.

The vast majority of the disposable absorbent articles of the aforementioned type have been designed to be disposed of in solid waste landfills. Such articles are delivered to landfills in their entirety along with fecal waste or urine contained on the used disposable articles. The unitary design of disposable articles has limited disposal options for consumers, and have not generally provided a sanitary means for the disposal of fecal material, such as by flushing the material down the toilet where it can be treated by the sewage system. This results in odor-causing fecal waste and bacteria being stored in the consumer's residence, child care centers, adult assisted living centers, or hospitals, prior to transporting the used disposable articles to the landfill. By directing used disposable articles to landfills, rather than to wastewater treatment facilities, fecal matter and bacteria may contaminate the groundwater in landfills and may spread diseases. Furthermore, the amount of disposable articles that have been discarded in landfills have led to the negative environmental impact that disposable articles have imposed on landfill capacity. The relatively few products that have been designed specifically to be disposed of by flushing, at least partially, suffer from a number of drawbacks.

A disposable article with a flushable insert is disclosed in U.S. Pat. Nos. 5,613,959; 5,458,591; 5,476,457; and 5,405,342 issued to T. H. Roessler et al. These patents disclose a disposable article incorporating a flushable insert positioned between a removable cover and a non-flushable garment shell. The insert includes a carrier sheet with bonded ends to encase absorbent material formed of wood pulp fluff and high-absorbency materials that absorb more than 25 times their weight in water. The garment shell includes a top bodyside liner that is liquid permeable and a liquid impermeable backsheet that are bonded along their entire periphery, with a secondary absorbent body of wood pulp fluff and high-absorbency materials between the top liner and backsheet, and the shell also includes containment flaps, and leg and waist elastic members. The cover is attached using peelable bonds along its periphery to the shell's top liner, and the insert is held in place between the cover and the shell's top liner. After use, the insert is removed to be flushed by breaking the peelable bonds of the cover to pull open the cover, and the remaining portions are not flushed which comprise the garment shell, and instead, are disposed in a landfill, composted or recycled. The patents do not anticipate and do not disclose the garment shell's top liner is torn open. The patents do not anticipate and teach against disposing a gap between an edge of the garment shell's top liner and backsheet for tearing open the garment shell, since the shell's leg and waist elastic members are attached to and positioned between the top liner and backsheet of the shell's edges, which inhibit a gap from being formed between the edges of the top liner and backsheet to tear open the shell.

A disposable article with a flushable absorbent insert is disclosed in U.S. Pat. No. 6,623,466 issued to I. Richardson. This patent discloses a disposable absorbent article that includes a disposable diaper shell consisting of a liquid permeable top liner to a liquid impermeable backsheet that are permanently bound together in facing relation along their entire periphery, which does not include an absorbent core, and instead the diaper shell includes a flushable absorbent insert positioned between the top liner and backsheet. The insert includes an absorbent core encased by a liquid permeable outer liner using a releasable binding, and an adhesive fastening means, which attaches the insert to the backsheet to keep the insert from shifting out of place inside the diaper shell. Alternatively, the insert may be used independently, without the diaper shell, and in combination with a reusable diaper cover with the insert's adhesive fastening means attaching the flushable insert to the reusable diaper cover. After use, pulling tabs on the top liner and perforations are used to detach a removable portion of the top liner, to create an opening along the top liner of the diaper shell. After detaching the removable liner, the insert remains attached to the diaper shell with the fastening means, since the insert is always used with the fastening means. In order to release the insert's absorbent core, peeling tabs are used to open the insert along the insert's releasable binding. The patent does not anticipate and does not disclose that the pulling tabs and the peeling tabs are situated to provide sanitary placements for tearing open the article. The patent does not anticipate and does not disclose that a gap is disposed between an edge of the top liner and the backsheet to tear open the article, since the top liner and backsheet are permanently bound together in facing relation along their entire periphery, and therefore, the patent teaches against having a gap disposed between an edge of the top liner and the backsheet to tear open the article.

A diaper combination of a reusable diaper cover with a flushable insert is disclosed in U.S. Pat. No. 8,002,762 to S.

Allison-Rogers on Aug. 23, 2011, and sold as gDiapers. The Allison-Rogers patent discloses the same elements as those in U.S. Pat. No. 6,623,466 issued to I. Richardson on Sep. 23, 2003 in the aforementioned reference, such as a flushable insert used in combination with a reusable article, and a fastening means attaching the insert to the reusable article. The Allison-Rogers patent discloses a fastening means for the insert having an elasticized pouch with snap fasteners, Velcro, as well as an adhesive fastening means as used in the Richardson patent. The Richardson patent discloses the flushable insert is designed to be opened after use; however, the Allison-Rogers patent does not anticipate and does not disclose that the flushable insert is opened after use, and does not disclose that the insert includes ripping features.

A diaper combination of a reusable diaper cover with a flushable insert pad is disclosed in U.S. Pat. No. 5,207,662 to A. James. The reusable diaper cover has the same hour glass shape as the insert pad and a fence that is designed to house the pad insert to hold it in place within the reusable diaper cover. The insert pad comprises an absorbent core of fluff pulp and a super-absorbent polymer mix between two out layers of non-woven sheets, and a protruding absorbent dam formed of extra super-absorbent polymer mix filler for leakage containment and absorption. The insert pad has two parallel longitudinal lines of perforation that intersect the absorbent dam. The patent discloses that the insert pad is easily torn into three equal parts along the two parallel longitudinal lines of perforation, and "when torn the entire pad is conveniently flushed not requiring two steps" of "stripping off" the insert pad's outer layers, since "this process is time consuming". The dam also inhibits the outer layers from being detached from the insert; thus, the patent teaches against detaching the outer layers from the article to release the absorbent core.

A diaper having a detachable and flushable portion of the topsheet is disclosed in U.S. Pat. No. 3,842,838 to D. A. Gellert. This patent discloses a disposable diaper comprising an absorbent pad between a liquid permeable top liner and a liquid impermeable backsheet. The top liner includes perforations to remove a portion of the top liner to flush. The patent discloses that diaper remainder is not flushed and is disposed separately, which includes the "strong" absorbent pad bonded to the backsheet. The patent teaches against a "weak" absorbent pad that may be released and flushed after detaching the top liner, disclosing that the invention "eliminates the need to have a weak water-dispersible absorbent pad".

A diaper pad that is intended to be completely disposed of in a toilet is disclosed in U.S. Pat. No. 3,211,147 to P. O. Pherson et al. discloses. The diaper pad includes a paper web outer wrapper, absorbent core comprising wood pulp fluff pads, and paper reinforcing strips. The outer wrapper encases the absorbent core. The absorbent core includes parallel embossed channels to distribute fluids. The wrapper and absorbent core are joined along waist-side edges and embossed using the paper reinforcing strips to form a rigid waist band that is strong enough to permit the use of safety pins. The outer wrapper is also embossed to the absorbent core longitudinally to allow the diaper to be folded along the parallel channels to contour the diaper with pleats that are embossed in place. After use, the user begins tearing at the embossed paper reinforcing strip of the waist band and along tearing lines formed from the absorbent core's inner parallel channels. The patent does not disclose that the outer wrapper includes ripping features. Further, the invention design inhibits detaching the outer wrapper from the insert, and inhibits releasing the absorbent core, since the absorbent core is embossed to the waist band and to the outer wrapper along the longitudinal channels, as well as confined inside the pleated folds.

These attempts to provide disposable articles that are detachable and flushable have not been entirely successful. Some of the disposable articles are complex and involve multiple steps to detach and flush the various components. Other articles are ineffective at significantly reducing the amount of materials disposed in the landfill. The disposal process has the potential of being unsanitary on the user's hands while handling the flushable components after use. With articles using high-absorbency materials, there exists potential to clog the toilet depending on the article's size and the toilet's flushing capability. In addition, contamination of the water supply may occur when flushing high-absorbency materials made from synthetic or inorganic materials. Further, many of these absorbent articles use elaborate designs requiring additional components to provide features that allow the articles to be detached and flushed. The additional components include: removable flushable inserts, fastening adhesives for inserts, elastic pouches for inserts, customized reusable diaper covers for the accompanying inserts, absorbent dams for inserts, channels to distribute fluids, pleats to form absorbent barriers, removable covers, and secondary absorbent bodies. The addition of these features presents numerous difficulties that increase the expense and complexity of production.

The production of disposable absorbent articles is generally considered a capital-intensive business. This is a consequence of the complex machinery required to manufacture product from incoming material streams at economically-feasible production rates. Any innovation that adds components or materials to the product produced, consequently increases material costs and complexity of production, which corresponds to increasing per-article costs for the manufacturer, and consequently, this additional cost is passed on to the consumer.

SUMMARY

In one embodiment of the present disclosure, a disposable absorbent article may comprise a liquid permeable top liner that may be partially or completely detached from the article after use to release the absorbent core from the article. The detachable design of the article allows the user to select among several disposal options for each of the detached components of the article based upon the user's preferences and particular circumstances, such as flushing down a toilet or septic tank, composting, recycling, or disposing in a landfill. This provides the user with the option of directing the solid fecal waste and a significant portion of the absorbent article to a wastewater treatment facility, rather than to a landfill. Consequently, this reduces or eliminates the amount of bacteria and odor-causing waste from the used disposable articles that must be stored by the user prior to disposing in the landfill. This also mitigates the impact on the environment, by reducing the amount of material and waste that is delivered to the landfill, and reduces the potential for fecal matter and bacteria to contaminate the groundwater in landfills.

The present disclosure was developed in order to remedy the previously-mentioned drawbacks associated with present disposable absorbent articles. This disclosure provides a disposable absorbent article that may be easily incorporated into the design of existing disposable articles to produce a detachable and flushable absorbent article. Some of the benefits include: simple to use, cost effective to produce, minimal modifications and materials required to produce, sanitary for the user to maneuver, mitigation of toilet clogging potential, significant reduction or elimination of materials and bacteria disposed in the landfill, and disposal options for the consumer.

BRIEF DESCRIPTION OF THE DRAWINGS

The foregoing and other objects, features and advantages of the present disclosure will become more apparent and better understood by reference to the following descriptions of non-limiting embodiments of the disclosure taken in conjunction with the accompanying drawings, wherein:

FIG. 6 is a perspective view of a further step in disposal of disposable absorbent article of FIG. 2.

FIG. 6A is a cross-sectional view taken along line 6A-6A of FIG. 6.

FIG. 6B is a cross-sectional view taken along line 6B-6B of FIG. 6.

FIG. 6C is a cross-sectional view taken along line 6C-6C of FIG. 6.

FIG. 8 is a perspective view of a step in disposal of disposable absorbent article of FIG. 7.

FIG. 8A is a cross-sectional view taken along line 8A-8A of FIG. 8.

FIG. 8B is a cross-sectional view taken along line 8B-8B of FIG. 8.

FIG. 8C is a cross-sectional view taken along line 8C-8C of FIG. 8.

FIG. 9 is a perspective view of a further step in disposal of disposable absorbent article of FIG. 7.

FIG. 9A is a cross-sectional view taken along line 9A-9A of FIG. 9.

FIG. 9B is a cross-sectional view taken along line 9B-9B of FIG. 9.

FIG. 9C is a cross-sectional view taken along line 9C-9C of FIG. 9.

DETAILED DESCRIPTION

Various non-limiting embodiments of the present disclosure will now be described to provide an overall understanding of the principles of the structure, function, use, and disposal options of the disposable absorbent articles. One or more examples of non-limiting embodiments of the present disclosure will be further illustrated in the description below and in the Figures. Those of ordinary skill in the art will understand that the features illustrated or described in connection with one non-limiting embodiment may be combined with other features of other non-limiting embodiments. Further, alternative absorbent materials may be substituted for those described herein. Such modifications and variations are intended to be included within the scope of the present disclosure. Nothing in this description should be, however, considered limiting the scope of the claims.

The disposable absorbent article of the present disclosure is utilized for absorption and containment of urine and other body exudates, such as disposable diapers, disposable training pants, disposable inserts, disposable absorbent pads, disposable incontinence articles, feminine care pads, and the like, which are used by infants, children, and adults. The detachable design of the article allows the user to select among several disposal options for each of the detached components of the disposable absorbent article based upon the user's preferences and particular circumstances, such as flushing down a toilet or septic tank, composting, recycling, or disposing in a landfill. For simplicity, the disposable absorbent article of this disclosure may also be referred to as the article.

Figure 1:
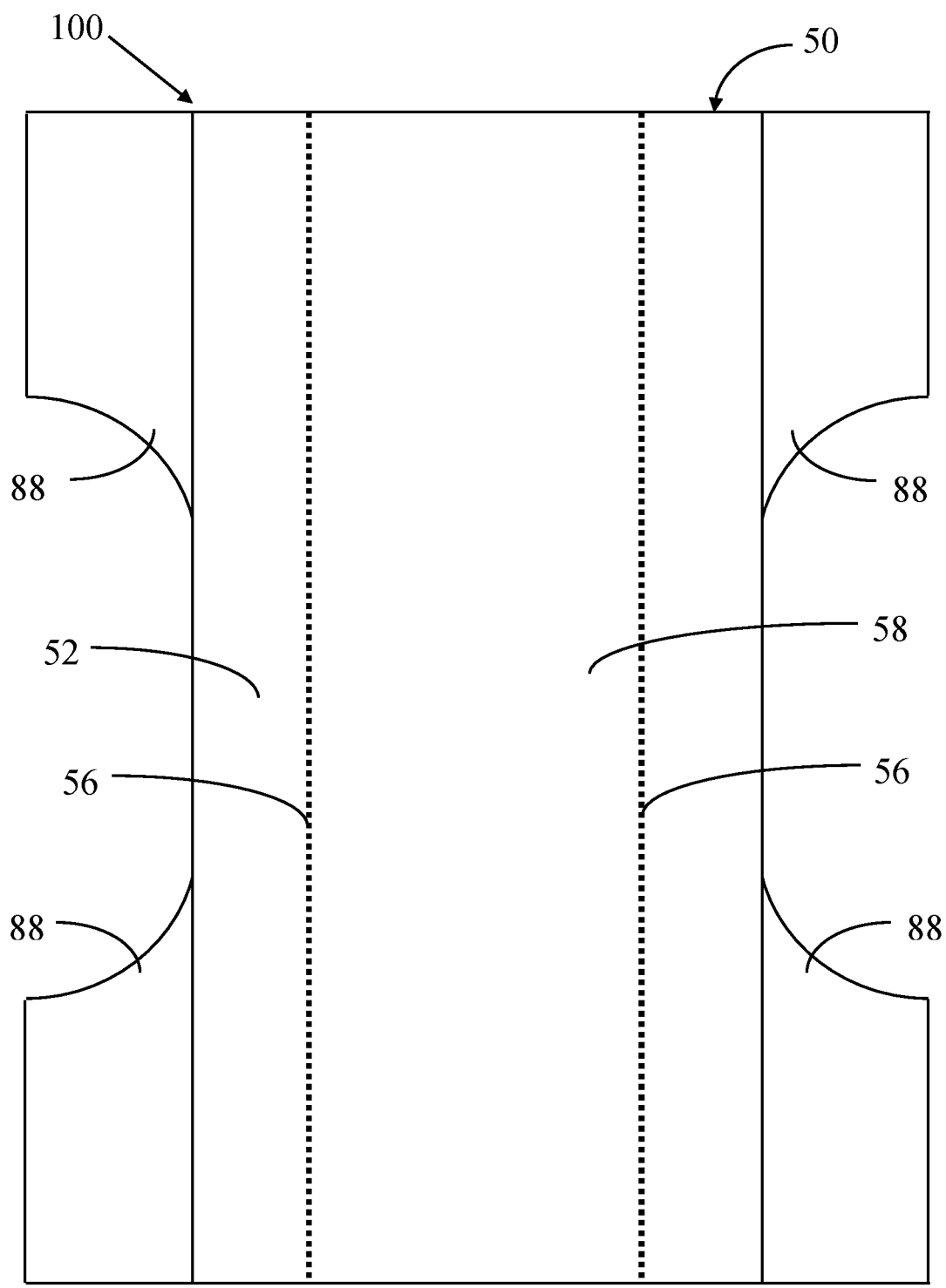
FIG. 1 is a top plan view of one embodiment of the disposable absorbent article.
Figure 2:
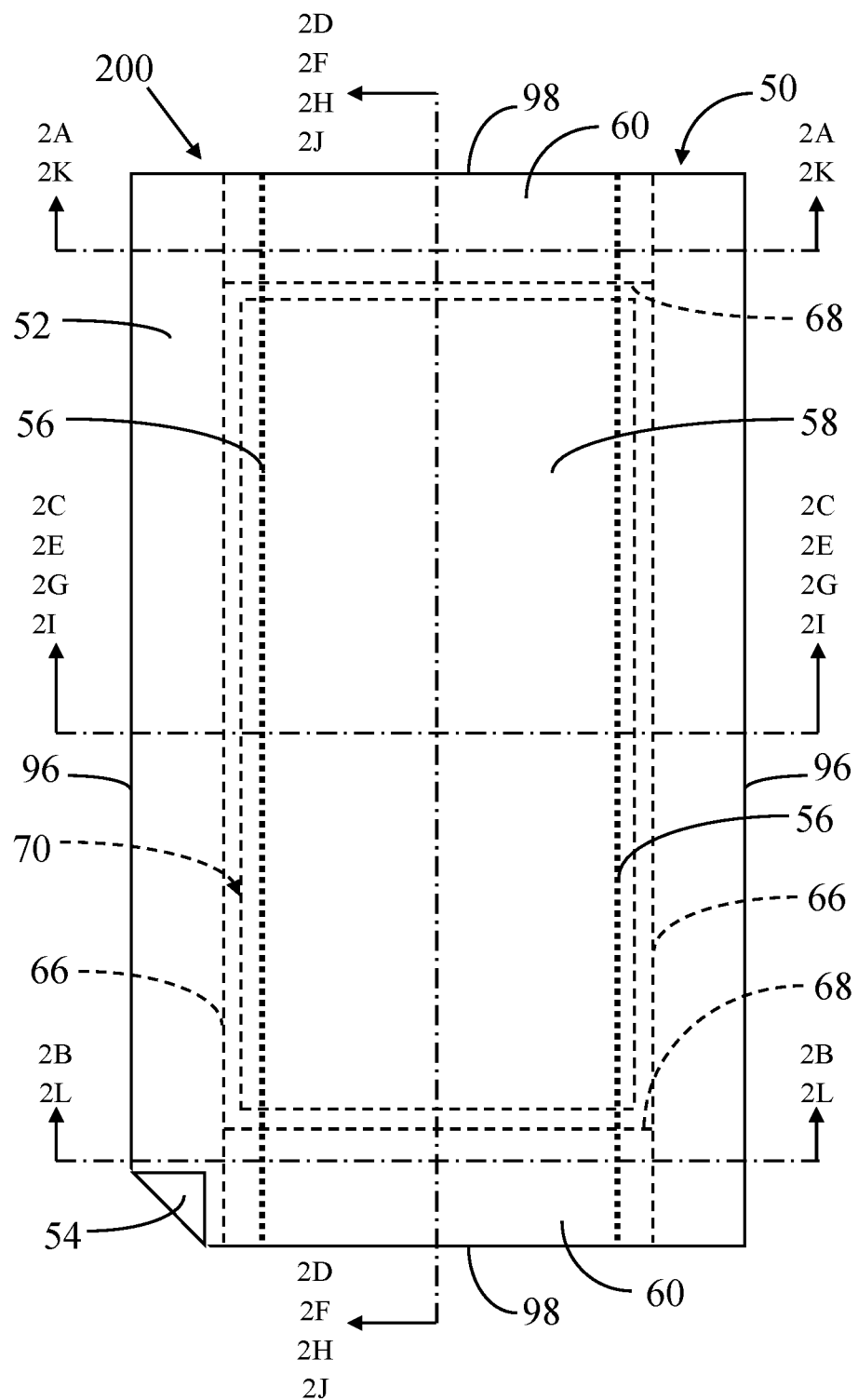
FIG. 2 is a top plan view of another embodiment of the disposable absorbent article with hidden lines to show interior construction and having a corner folded back to show exterior construction.

FIG. 1 depicts an embodiment illustrated as article 100, and shows that article 100 may be formed of an absorbent body 50 designed for the absorption and containment of urine and other body exudates. Absorbent body 50 may comprise a top liner 52 that may incorporate a removable liner 58 formed as a removable portion of top liner 52. The surface of top liner 52 may incorporate ripping feature 56 utilized to tear and separate the removable liner 58 from top liner 52. The ripping feature 56 may comprise two parallel lines of relative weakness, or series of perforations, which may be incorporated along top liner 52 throughout the length of article 100. Ripping feature 56 defines the periphery of removable liner 58 and is shown to form a rectangular-shaped removable liner 58 the length of article 100; although it is readily apparent that the ripping feature 56 may employ various configurations, shapes, sizes, or placements. In some circumstances it may be desired to include fastener sections 88 that may be formed of a material integral to absorbent body 50, may comprise separate components attached to absorbent body 50, or may be omitted. Fastener sections 88 may include attachment components (not represented) to secure article 100 for use of a wearer. Article 100 is shown having a shape configuration that is I-shaped; although, it is readily apparent that other shapes may also be utilized, such as: rectangular, hourglass, elliptical, T-shape, or any other suitable shape based upon the design requirements. FIG. 2 will describe interior construction of absorbent body 50.

The embodiment of FIG. 2 depicts article 200 that may be partially flushable, compostable, and biodegradable. Article 200 may be formed of an absorbent body 50 without fastener sections 88; it is readily apparent that fastener sections 88 may be included. Article 200 is shown with hidden lines to show the interior construction and a corner folded back to show the exterior construction.

FIG. 2 depicts an embodiment illustrated as article 200 that shows top liner 52 and backsheet 54 may be bonded by leg seams 66 and waist seams 68, using methods and materials described for bonding 64, below. Top liner 52 and backsheet 54 may extend beyond the ends of the absorbent core 70. Hidden lines show the outline of an absorbent core 70 positioned between top liner 52 and the backsheet 54. Absorbent core 70 refers to the element of article 200 having a substantial absorbent capacity.

Along the surface of top liner 52 may be incorporated ripping feature 56 to facilitate separating the removable liner 58 from top liner 52. The ripping feature 56 comprises two parallel lines of relative weakness, or series of perforations, which may be incorporated along top liner 52 throughout the length of article 200; although it is readily apparent that the ripping feature 56 may employ various configurations, shapes, sizes, or placements. Removable liner 58 and ripping feature 56 are shown positioned within the area between the leg seams 66. Sanitary grips 60 are the ends of removable liner 58 that may extend beyond the waist seams 68. Article 200 is shown having a rectangular shape; although, it is readily apparent that other shapes may also be utilized based upon design requirements.

Top liner 52 is generally the wearer-facing surface. It may be desired that material forming top liner 52 may be compliant, soft feeling, and nonirritating to the wearer's skin. The top liner 52 may be a flexible, porous sheet which is liquid permeable permitting liquids to readily penetrate through its thickness. The top liner 52 may be formed of a material that contains bodily excrements and may have a pore size that readily allows the passage of liquids, such as urine.

A suitable top liner 52 may be manufactured from a wide range of materials, such as natural fibers, synthetic fibers, or a combination of natural and synthetic fibers. The top liner 52 may comprise materials ordinarily used in the art, for example, a nonwoven web or sheet of wet strength tissue paper, a spunbonded, meltblown or bonded-carded web, or a web of natural polymer filaments such as rayon or cotton. Top liner 52 may be fabricated from a material that is flushable through a sewer or septic system, and may be biodegradable and compostable to breakdown over a relatively short period of time when exposed to natural elements such as air, heat and moisture that can accelerate the degrading process once discarded.

Removable liner 58 may be formed of the same material as top liner 52. Removable liner 58 may be substantially fluid permeable material that may be flushable, biodegradable, and compostable.

Backsheet 54 is generally the garment-facing surface. It may be desired that backsheet 54 may be formed of a thin, flexible, compliant, and liquid impermeable material that prevents the exudates absorbed and contained therein from wicking through to the clothing, bed sheet, and/or the environment of the wearer. Backsheet 54 may comprise materials ordinarily used in the art, for example, a web or sheet of plastic film such as thermoplastic film, or other suitable materials. Alternatively, the backsheet 54 may comprise a nonwoven, fibrous web which has been suitably constructed and arranged to be substantially liquid impermeable, or backsheet 54 may be omitted entirely. Other suitable materials may include breathable materials which permit vapors to escape while still preventing exudates from passing through the backsheet 54. Backsheet 54 may be substantially opaque or transparent, and may have an embossed or matte surface.

Absorbent core 70 may comprise materials that are generally compressible, comfortable, non-irritating to the wearer's skin, and capable of absorbing and retaining liquids and certain body exudates. The total absorbent capacity and size of the absorbent core 70 is dictated by the absorbency requirements and can be varied to accommodate wearers ranging from infants through adults. Furthermore, the total absorbent capacity of the absorbent core 70 should be compatible with the design exudates loading in the intended use of the article 200. Absorbent core 70 may be flushable, biodegradable, and compostable.

Bonding 64 comprises conventional methods and materials used in the art to join together adjacent layers and components. Sufficient examples for bonding 64 may comprise spraying adhesive on the whole or part of the surface, using a uniform continuous layer of adhesive, a patterned layer of adhesive, an array of separate lines or spots of adhesive, or a combination thereof. Alternatively, the attachment methods and materials may comprise using adhesives, heat bonds, pressure bonds, ultrasonic bonds, mechanical bonds, embossing, or any other suitable attachment methods or combinations of these attachment methods known to those in the art. The terms "join" or "bond" or "attach", as used herein, are interchangeable and encompasses configurations whereby elements may be affixed directly or indirectly employing conventional techniques such as those well known in the art.

Leg seams 66 and waist seams 68 are integral portions of the seams joining top liner 52 and backsheet 54 using bonding 64, and are located where backsheet 54 and top liner 52 are joined together proximate to the leg-side edge 96 and waist-side edge 98 that are in contact with the wearer's legs and waist, respectively. Alternatively, waist seams 68 may use a method or material for bonding 64 that may allow the user to detach sanitary grips 60 rather easily when pulled. Leg seams 66 may be substantially straight, or may be partly or fully curved (not shown). In some circumstances it may be desired that leg seams 66 and waist seams 68 include elastic elements (not represented) to provide improved fit and to conform the shape of the wearer and minimize the potential for leakage. Alternatively, leg elastic elements (not represented) for fluid containment and improved leakage protection may be utilized and may be attached superimposed throughout the length of the surface of top liner 52 parallel to leg seams 66 and may extend outward from removable liner 58.

Ripping feature 56 may be incorporated along the surface of top liner 52 to facilitate detaching the removable liner 58 from top liner 52. Ripping feature 56 may comprise perforations, lines of relative weakness, cuts, holes, openings, slits, notches, as well as areas on or attached to top liner 52 that may be weakened by ultrasonics, embossing, adhesives, or other suitable means to open, tear, sever, separate or detach a substantial portion of top liner 52 and that may be used to facilitate in detaching the article. The ripping feature 56 of article 200 shown in FIG. 2 comprises two parallel lines of relative weakness, or series of perforations, which may be incorporated along top liner 52 throughout the length of article 200; it is readily apparent that the ripping feature 56 may employ various configurations, sizes, placements, or may be omitted entirely. This simple configuration for the ripping feature 56 may allow the manufacturer the option to utilize a material that is pre-perforated for top liner 52 prior to the assembly process of article 200, rather than during, which may minimize the modifications and cost requirements for retrofitting existing equipment and processes necessary to apply ripping features 56 to top liner 52 during the assembly process of article 200.

Sanitary grips 60 may be integral extensions of top liner 52 comprising ends of the removable liner 58 that are unattached to backsheet 54. Sanitary grips 60 may extend beyond the waist seams 68, and as a result of their distance from exudation points, are less likely to be soiled at the time replacement of article 200 becomes necessary or desirable.

After use, sanitary grips 60 may provide a sanitary placement for handling removable liner 58, and enable the user to grasp removable liner 58 proximate to one or both ends of article 200 and detach removable liner 58 from top liner 52 with the optimum level of ease and convenience to the user.

FIGS. 2A to 2L depict cross-sectional views showing various alternatives for the interior construction of article 200 shown in FIG. 2. As shown in most of the depictions along the centerline of the width of article 200, the surface of the top liner 52 may incorporate ripping feature 56 to facilitate in separating the removable liner 58 from top liner 52. Various alternatives for the interior construction of article 200 between the top liner 52 and backsheet 54 are depicted in the cross-sectional views that follow.

Figure 2A:
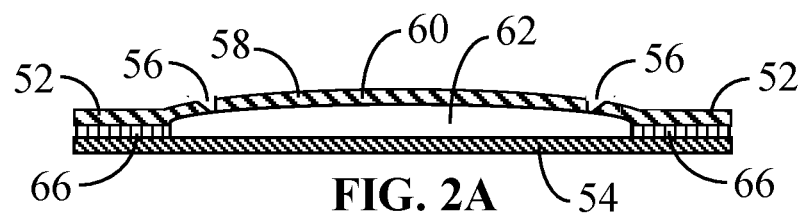
FIG. 2A is a cross-sectional view taken along line 2A-2A of FIG. 2.
Figure 2B:
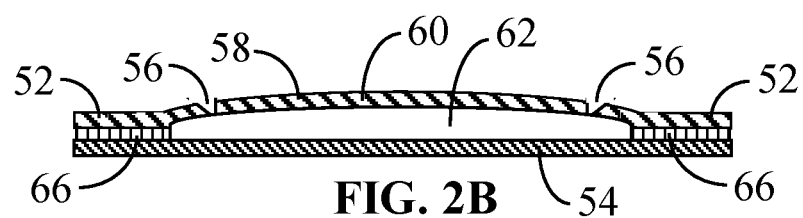
FIG. 2B is a cross-sectional view taken along line 2B-2B of FIG. 2.

FIGS. 2A and 2B depict cross-sectional views that show the interior construction along the two ends of article 200 that extend beyond the waist seams 68 toward the waist-side edge 98 and show a sanitary gap 62. Sanitary grips 60 are shown to be integral extensions of top liner 52 and the ends of the removable liner 58 that are unattached to backsheet 54 to form gap 62. Since the user's waste is confined inside the absorbent core 70 within the region between leg seams 66 and waist seams 68, and since gap 62 extends beyond the waist seams 68 toward the waist-side edge 98 of article 200, which is outside of the exudation region, gap 62 is less likely to be soiled at the time replacement of article 200 becomes necessary or desirable. The open space of the gap 62 between top liner 52 and backsheet 54 provides a sanitary placement for the user's hand to grasp sanitary grip 60 proximate one or both ends of article 200 to detach removable liner 58 from top liner 52 with the optimum level of ease and hygienic convenience. Top liner 52 may incorporate ripping features 56 to facilitate detaching the removable liner 58.

The cross-sectional views of FIGS. 2C to 2J show that top liner 52 and backsheet 54 may be joined by leg seams 66 and waist seams 68 to form an envelope-like enclosure for the absorbent core 70. The top liner 52 is shown positioned adjacent the body surface of absorbent core 70 so that liquid exudates are discharged onto and penetrate through top liner 52 where they are absorbed by the absorbent core 70. The absorbent core 70 also may comprise one or more sheets of dispersal layer 72, or dispersal layer 72 may be omitted. A sheet of dispersal layer 72 may be positioned between top liner 52 and absorbent core 70, or absorbent core 70 may be disposed between two sheets of dispersal layers 72. The cross-sectional views of FIGS. 2D, 2F, 2H, 2J show that sanitary grips 60 may be unattached to backsheet 54 to form the opened space of the sanitary gap 62 along the two ends that extend beyond the waist seams 68, as a result of their distance from exudation points, are less likely to be soiled.

Figure 2C:
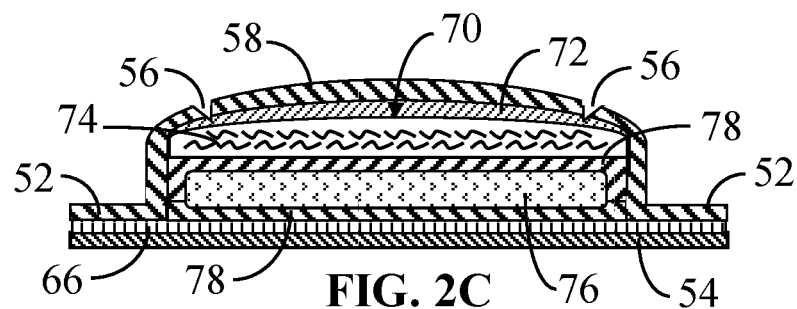
FIG. 2C is a cross-sectional view taken along line 2C-2C of FIG. 2.
Figure 2D:
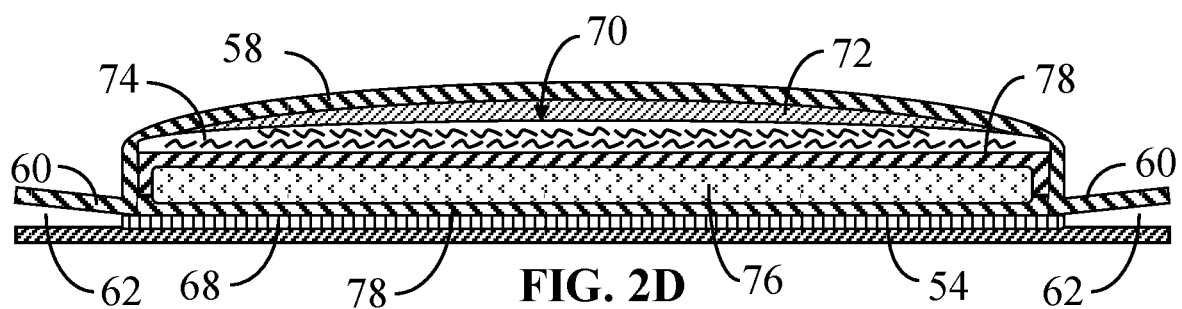
FIG. 2D is a cross-sectional view taken along line 2D-2D of FIG. 2.

FIGS. 2C and 2D depict cross-sectional views along the centerlines of the width and length, respectively, showing the interior construction of an embodiment of article 200. Top liner 52 and backsheet 54 are shown forming an envelope-like enclosure for the absorbent core 70 that may comprise absorbent material 74. Membrane 78 may be positioned between the absorbent core 70 and high-absorbency material 76 to separate high-absorbency material 76 from absorbent core 70, or membrane 78 may wrap around to encase high-absorbency material 76. Membrane 78 may be attached to backsheet 54 to encase and secure high-absorbency material 76 between membrane 78 and backsheet 54.

Figure 2E:
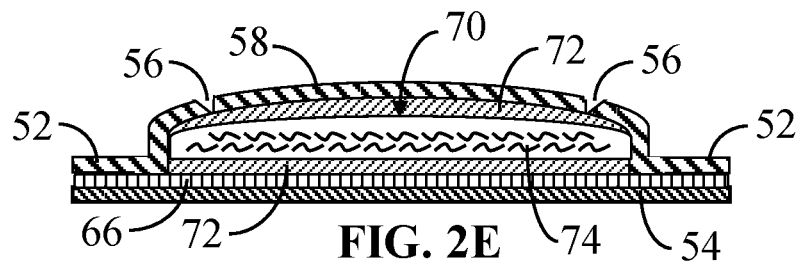
FIG. 2E is a cross-sectional view taken along line 2E-2E of FIG. 2.
Figure 2F:
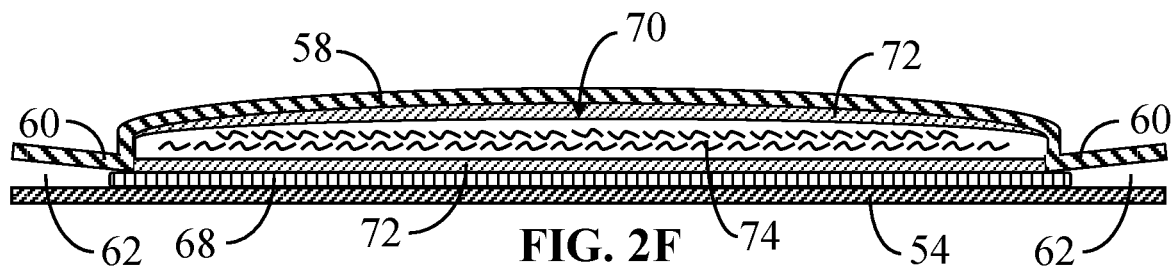
FIG. 2F is a cross-sectional view taken along line 2F-2F of FIG. 2.

FIGS. 2E and 2F depict cross-sectional views along the centerlines of the width and length, respectively, showing the interior construction of an alternative embodiment of article 200. Top liner 52 and backsheet 54 are shown forming an envelope-like enclosure for absorbent core 70. The absorbent core 70 may comprise absorbent material 74.

Figure 2G:
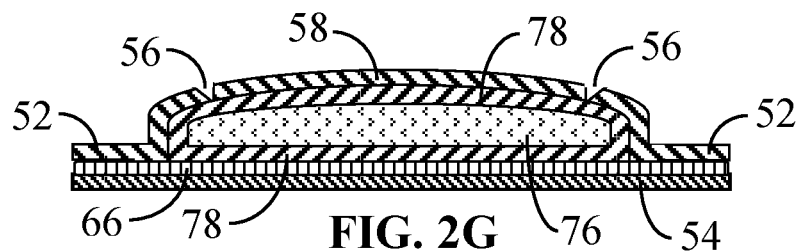
FIG. 2G is a cross-sectional view taken along line 2G-2G of FIG. 2.
Figure 2H:
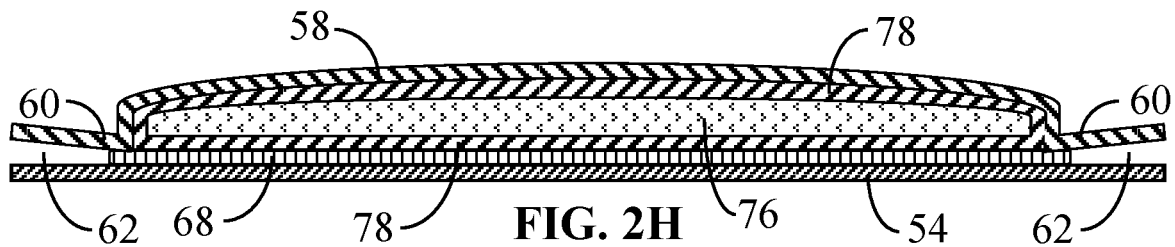
FIG. 2H is a cross-sectional view taken along line 2H-2H of FIG. 2.

FIGS. 2G and 2H depict cross-sectional views along the centerlines of the width and length, respectively, showing the interior construction of another alternative embodiment of article 200. Top liner 52 and backsheet 54 are shown forming an envelope-like enclosure for membrane 78 and high-absorbency material 76. Top liner 52 may be positioned adjacent to membrane 78 so that liquid exudates are discharged onto and penetrate through the top liner 52 and membrane 78 where they are absorbed by the high-absorbency material 76. Membrane 78 may be attached to backsheet 54 to secure high-absorbency material 76 between membrane 78 and backsheet 54. Membrane 78 may also wrap around to encase high-absorbency material 76, and may be attached to backsheet 54.

Figure 2I:
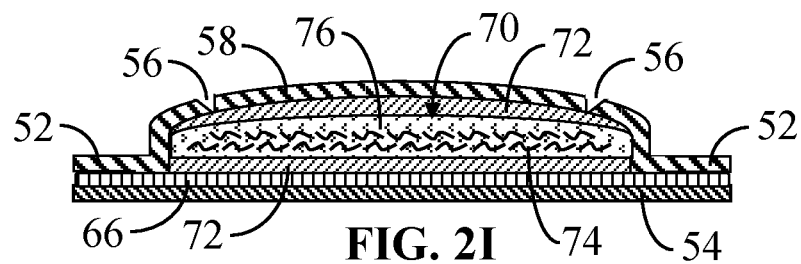
FIG. 2I is a cross-sectional view taken along line 2I-2I of FIG. 2.
Figure 2J:
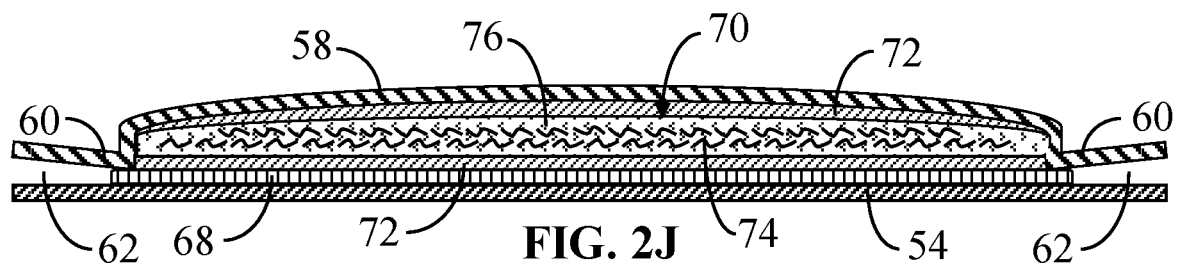
FIG. 2J is a cross-sectional view taken along line 2J-2J of FIG. 2.

FIGS. 2I and 2J depict cross-sectional views along the centerlines of the width and length, respectively, showing the interior construction of an example of another alternative embodiment of article 200. Top liner 52 and backsheet 54 are shown forming an envelope-like enclosure for the absorbent core 70. The absorbent core 70 may comprise absorbent material 74 combined with high-absorbency material 76.

Figure 2K:
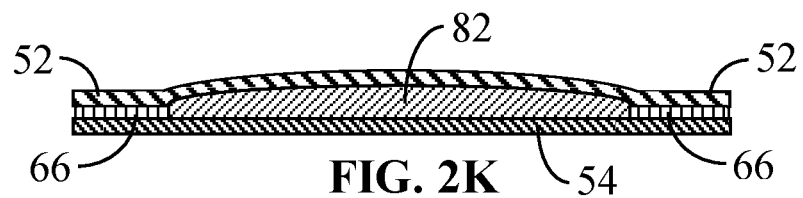
FIG. 2K is a cross-sectional view taken along line 2K-2K of FIG. 2.
Figure 2L:
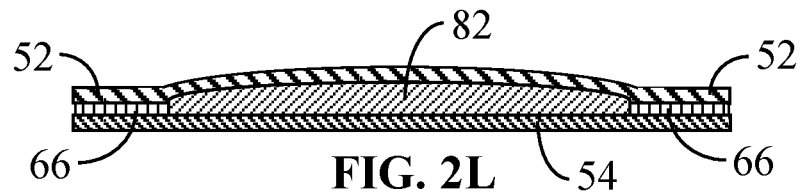
FIG. 2L is a cross-sectional view taken along line 2L-2L of FIG. 2.

FIGS. 2K and 2L depict cross-sectional views showing alternative embodiments of the interior construction along the two ends of article 200 that may extend beyond waist seams 68 toward the waist-side edge 98. In some circumstances it may be desired that waist features 82 may be used as an alternative to gap 62. The waist feature 82 may comprise a bonded seam as described for bonding 64. Optionally, waist features 82 may include elastic elements to provide an improved fit for the wearer and minimize the potential for leakage, which may be attached between top liner 52 and backsheet 54 or may be attached to top liner 52 or to backsheet 54.

Absorbent core 70 may comprise absorbent material 74, or may comprise absorbent layers superposed in facing relation, such as dispersal layer 72 and absorbent material 74. Optionally, absorbent core 70 may also include high-absorbency material 76.

The dispersal layer 72 improves the tensile strength of absorbent core 70 and reduces the tendency for it to split, lump or ball when wetted. Dispersal layer 72 improves lateral wicking of the absorbed exudates, thereby providing a more even distribution of absorbed human exudates throughout the absorbent core 70. The materials used to form dispersal layer 72 may comprise materials ordinarily used in the art, for example, wet-strength cellulosic material, wet strength tissue paper, or creped wadding. Alternatively, dispersal layer 72 may be formed from the same material used for top liner 52, or the dispersal layer 72 may be omitted. Dispersal layer 72 may be attached to components of article 200 as described for bonding 64. Dispersal layer 72 may be fluid permeable, flushable, biodegradable, and compostable.

Absorbent material 74 may be a material that has some absorbency property or liquid retaining properties formed from materials that are generally compressible, comfortable, non-irritating to the wearer's skin, and capable of absorbing and retaining liquids and certain body exudates. Absorbent material 74 may be formed from materials ordinarily used in the art, for example, such as wood pulp fluff, airfelt, airlaid, cellulose fiber, creped cellulose wadding, tissue, organic materials, or any other known absorbency materials or combinations of materials. Absorbent material 74 may be flushable, biodegradable, and compostable.

High-absorbency material 76 may be employed to enhance absorption capacity and to reduce the overall size or thickness of the absorbent core 70, and thereby improve wearer comfort and reduce the volume of disposable waste created by a soiled article 200. The high-absorbency material 76 used in the art is capable of absorbing at least 15 times to more than 25 times its weight in water. The high-absorbency material 76 may comprise materials ordinarily used in the art that comprise compounds to increase the absorbency of the body, for example, an effective amount of organic materials, or inorganic highly-absorbent materials. Sufficient high-absorbency materials 76 may also be formed of natural materials that are used in the art, as well as synthetic materials, such as super-absorbent polymers. The high-absorbency material 76 may also be formed of biodegradable highly-absorbent materials formed from degradable substances. High-absorbency material 76 may comprise a discrete layer separate from the absorbent material 74. Alternatively, high-absorbency material 76 may be combined to be integral with absorbent material 74, or high-absorbency material 76 may be omitted entirely.

Since typical high-absorbency materials 76 known in the art are capable of absorbing up to 25 times their weight in water, membrane 78 may be utilized to reduce the risk of clogging the toilet after use, by creating a barrier that isolates and prevents high-absorbency material 76 from being released and flushed. In addition, membrane 78 may create a barrier to prevent high-absorbency materials 76 from escaping from the interior of article 200 through perforations employed for ripping feature 56, to avoid high-absorbency material 76 from having direct contact with the wearer's skin during use. Membrane 78 may be formed from the same fluid permeable material used for the top liner 52. Membrane 78 may be coterminous with backsheet 54, or may be reduced in length and/or width while enclosing high-absorbency materials 76.

Figure 3:
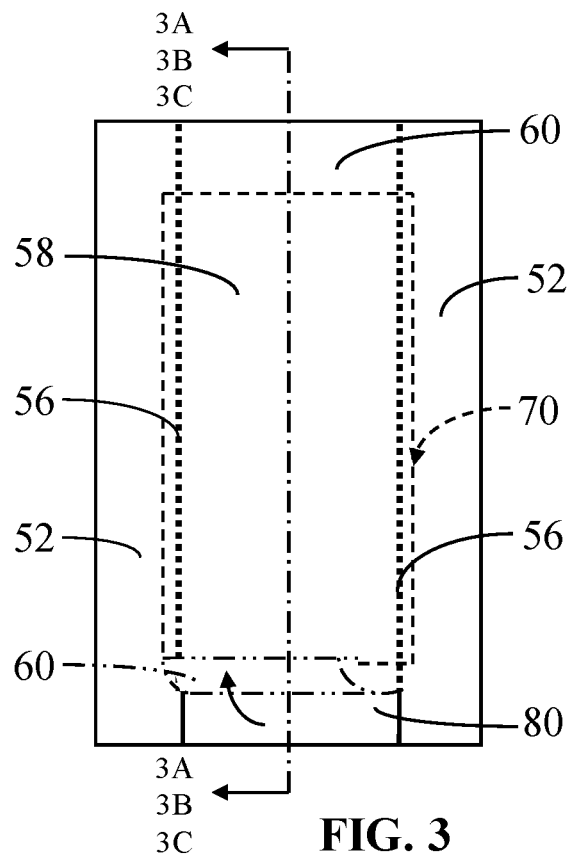
FIG. 3 is a perspective view of an initial step in disposal of disposable absorbent article of FIG. 2.

FIG. 3 shows the detachment operation of article 200 in preparation for disposal after use, which may be performed above a toilet. A sanitary grip 60 is shown detached from article 200. Sanitary grip 60 is of sufficient size and configuration to provide a means for the user to easily grasp removable liner 58 and to detach removable liner 58 from top liner 52 with the optimum level of ease and convenience. The user may pull on either of the sanitary grips 60 proximate to waist-side edge 98, or may pull on both sanitary grips 60 simultaneously, and tear along ripping feature 56 to detach removable liner 58 from top liner 52. Sanitary grips 60 allow the user to be better enabled to avoid contacting the wearer's exudates with the user's hands when detaching removable liner 58 from the top liner 52.

Figure 3A:
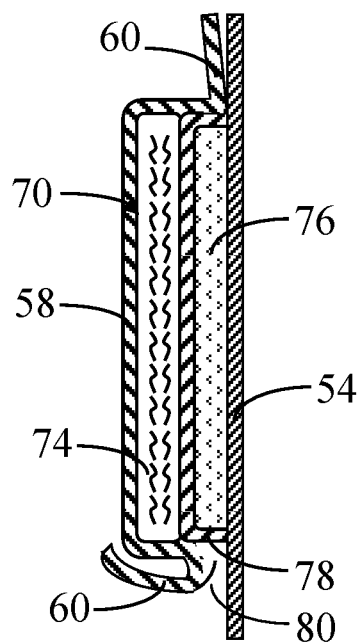
FIG. 3A is a cross-sectional view taken along line 3A-3A of FIG. 3.

FIG. 3A is a cross-sectional view of the detachment operation shown in FIG. 3. A sanitary grip 60 is shown being separated from article 200. The interior construction depicted in FIG. 2D is depicted comprising top liner 52 and backsheet 54 forming an envelope-like enclosure for absorbent core 70, membrane 78, and high-absorbency material 76. Membrane 78 may be positioned between absorbent core 70 and high-absorbency material 76, and may be attached to backsheet 54.

Figure 3B:
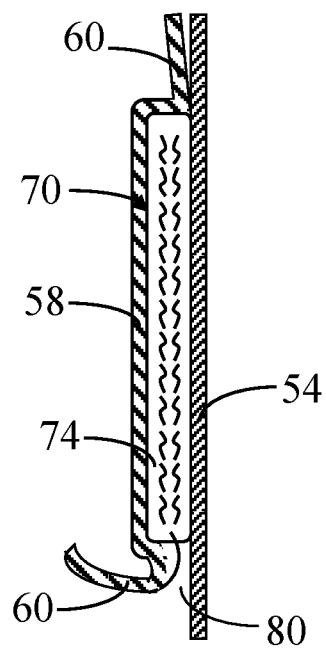
FIG. 3B is a cross-sectional view taken along line 3B-3B of FIG. 3.

FIG. 3B is an alternative cross-sectional view of the operation of article 200 shown in FIG. 3. Sanitary grip 60 is shown being separated from article 200. The interior construction from FIG. 2F is depicted comprising top liner 52 and backsheet 54 forming an envelope-like enclosure for the absorbent core 70. The absorbent core 70 may comprise absorbent material 74. The interior construction from FIG. 2J (not shown) comprising absorbent core 70 that combines absorbent material 74 and high-absorbency material 76 may be detached as shown in FIG. 3B.

Figure 3C:
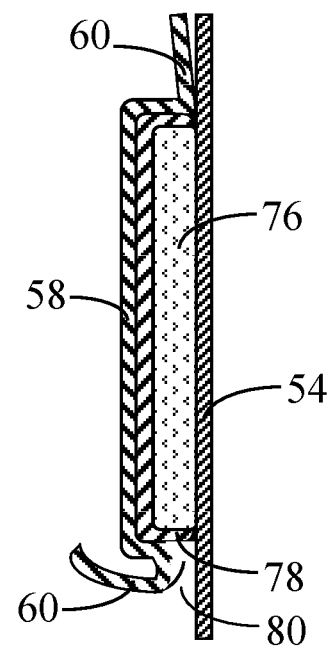
FIG. 3C is a cross-sectional view taken along line 3C-3C of FIG. 3.

FIG. 3C is another alternative cross-sectional view of the operation of article 200 shown in FIG. 3. A sanitary grip 60 is shown detached from article 200. The interior construction from FIG. 2H is depicted comprising top liner 52 and backsheet 54 forming an envelope-like enclosure for high-absorbency material 76 and membrane 78. Membrane 78 is attached to backsheet 54.

Figure 4:
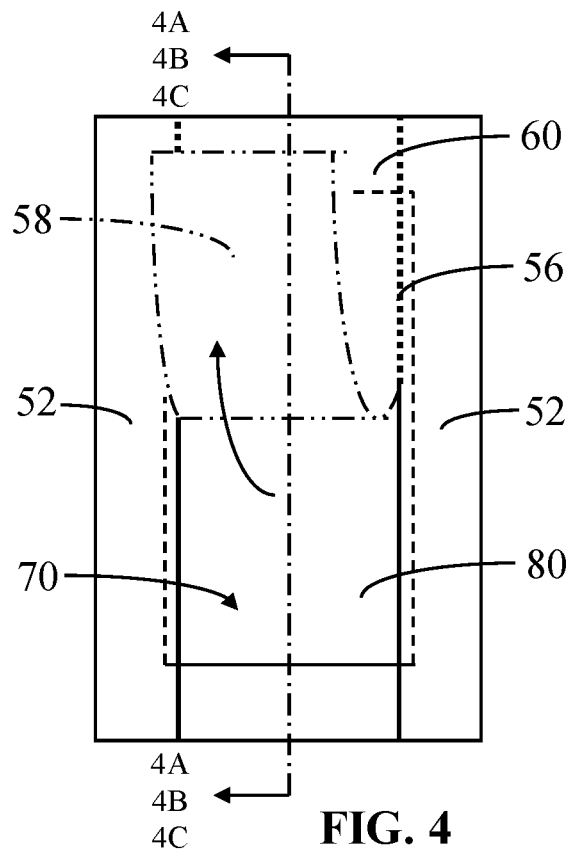
FIG. 4 is a perspective view of another step in disposal of disposable absorbent article of FIG. 2.

FIG. 4 shows the continuation of the detachment operation of article 200 in preparation for disposal after use. Removable liner 58 is shown partially detached from the top liner 52 of article 200. Absorbent core 70 is shown partially exposed within opening 80.

Figure 4A:
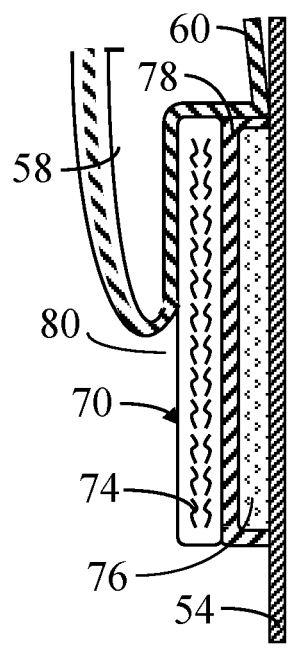
FIG. 4A is a cross-sectional view taken along line 4A-4A of FIG. 4.
Figure 4B:
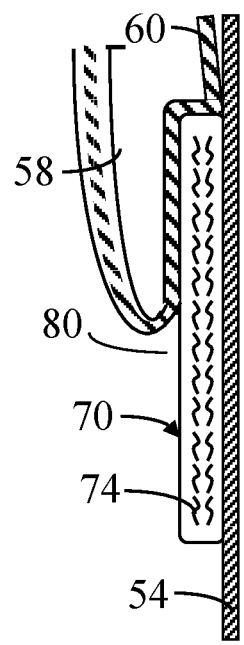
FIG. 4B is a cross-sectional view taken along line 4B-4B of FIG. 4.
Figure 4C:
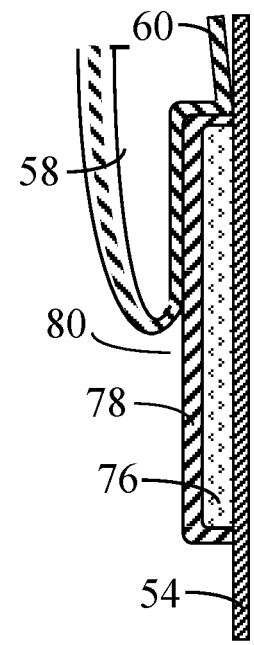
FIG. 4C is a cross-sectional view taken along line 4C-4C of FIG. 4.

FIGS. 4A, 4B, and 4C are cross-sectional views of article 200 in FIG. 4 showing removable liner 58 partially detached and comprise interior constructions of FIGS. 3A, 3B, and 3C, respectively. After use, removable liner 58 may be completely detached from article 200 and may be flushed in a toilet along with body exudates that may be contained on removable liner 58. It is readily apparent that removable liner 58 may also be partially detached to remain on article 200 to be composted or disposed in a landfill after use.

Figure 5:
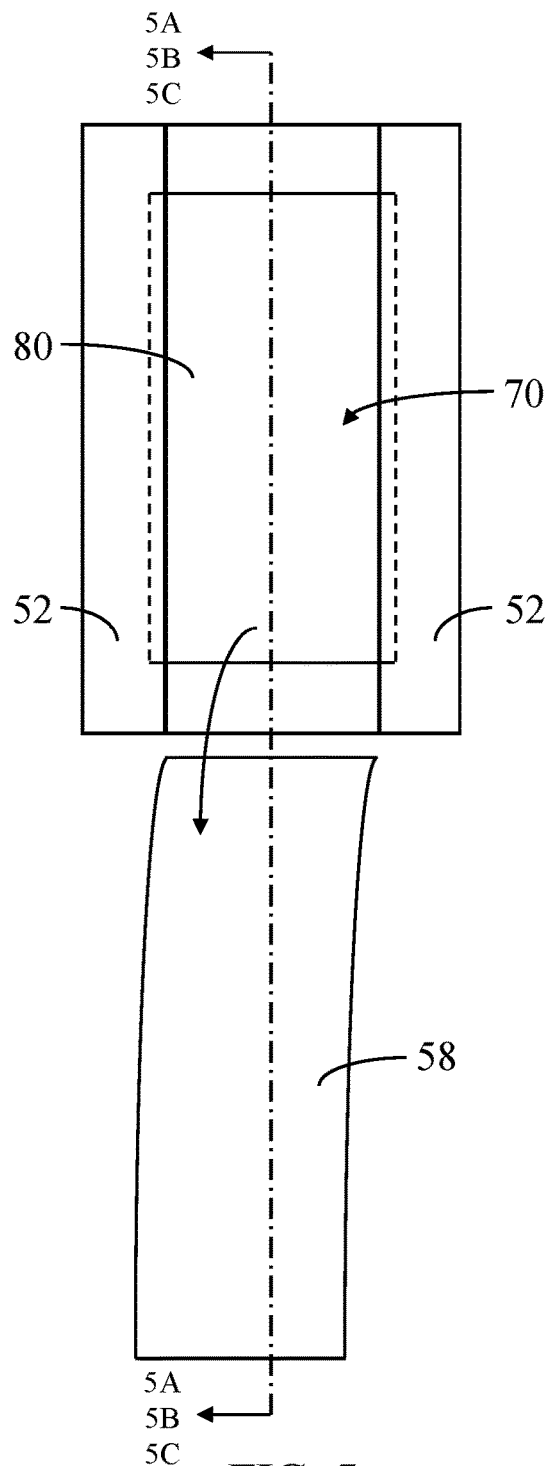
FIG. 5 is a perspective view of a further step in disposal of disposable absorbent article of FIG. 2.
Figure 5A:
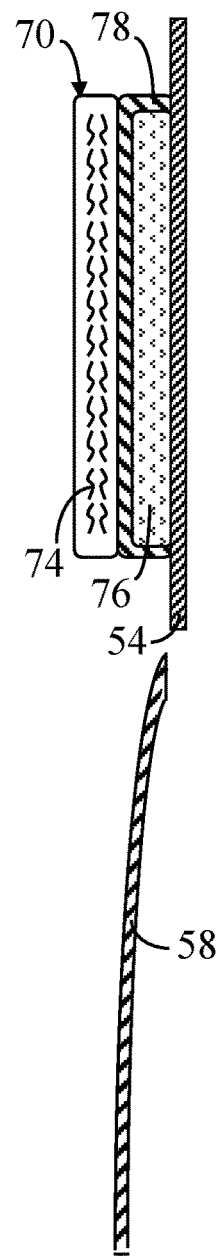
FIG. 5A is a cross-sectional view taken along line 5A-5A of FIG. 5.
Figure 5B:
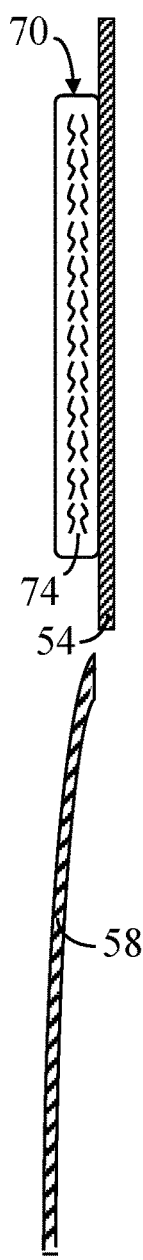
FIG. 5B is a cross-sectional view taken along line 5B-5B of FIG. 5.
Figure 5C:
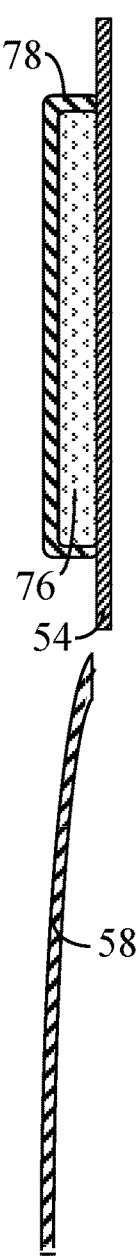
FIG. 5C is a cross-sectional view taken along line 5C-5C of FIG. 5.

FIG. 5 shows a subsequent step in the detachment operation of article 200 in the preparation for disposal after use, which may be performed above a toilet. Removable liner 58 is shown completely detached from article 200, which creates an opening 80 along the surface of the top liner 52. After being removed from article 200, removable liner 58 may be flushed along with body exudates that may be contained on removable liner 58. Absorbent core 70 is shown exposed within opening 80. FIGS. 5A, 5B, and 5C show cross-sectional views of article 200 in FIG. 5 comprising the interior constructions of FIGS. 4A, 4B, and 4C, respectively, and show that removable liner 58 is completely detached from article 200.

FIG. 6 depicts further steps in the detachment and disposal operations of article 200, which shows that after removable liner 58 has been removed opening 80 may allow absorbent core 70 to be released from interior of article 200. Article 200 may be inverted above a toilet to allow absorbent core 70 to fall by gravity into a toilet to be flushed in a toilet, or composted. Although, the absorbent core 70 is depicted as a whole unit, it may be in pieces after being released from article 200. Dispersal layer 72 may remain attached to article 200 or may be released after use. Hidden lines show outline of membrane 78 for FIGS. 6A and 6C.

Article remainder 86 comprises the shell of article 200 that remains after the removable liner 58 and absorbent core 70 have been removed from article 200. Article remainder 86 may comprise backsheet 54 and the portion of top liner 52 that remains attached to backsheet 54 after removable liner 58 has been removed, and any additional materials that may have been included with article 200, such as high-absorbency material 76, membrane 78, as well as any fastener sections 88 (not shown), attachment components (not shown), or elastic elements (not shown). Although high-absorbency material 76 may be expanded from the fluids that may have been absorbed therein during use, once the fluids dry and evaporate the high-absorbency material 76 will shrink back substantially close to the original size, which will reduce the amount of material discarded. After use, article remainder 86 may be recycled or disposed in a landfill.

FIG. 6A is the cross-sectional view of article 200 in FIG. 6 showing the interior construction of FIG. 5A. Absorbent core 70 is shown released from article 200, and may be flushed or composted after use. Article remainder 86 is shown comprising high-absorbency material 76 enclosed between membrane 78 and backsheet 54. After use, article remainder 86 may be recycled or disposed in a landfill.

FIG. 6B is the cross-sectional view of article 200 in FIG. 6 showing the interior construction of FIG. 5B. Absorbent core 70 may be released from article 200 as shown in FIG. 6B, and may be flushed or composted after use. Article remainder 86 is shown comprising backsheet 54, which may be recycled or disposed in a landfill after use. The interior construction from FIG. 2J (not shown) comprising absorbent core 70 that combines absorbent material 74 and high-absorbency material 76 may be detached as shown in FIGS. 3B, 4B, and 5B; absorbent core 70 may be released from article 200 as shown in FIG. 6B, and may be composted after use, or may be flushed if organic.

FIG. 6C is the cross-sectional view of article 200 in FIG. 6 showing article remainder 86 comprising the interior construction of FIG. 5C. Article remainder 86 is shown comprising the high-absorbency material 76 enclosed between membrane 78 and backsheet 54. After use, article remainder 86 may be recycled or disposed in a landfill.

Figure 7:
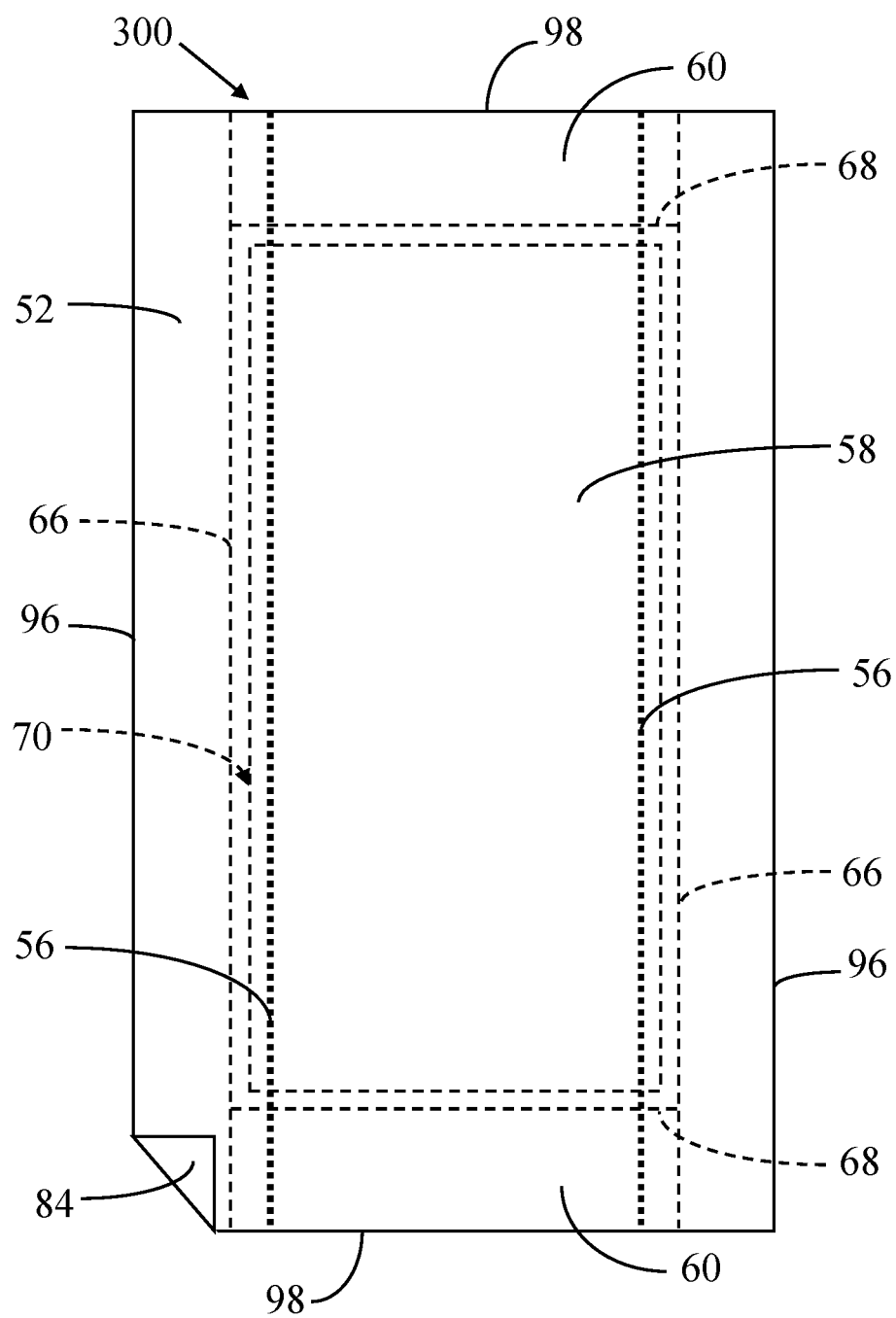
FIG. 7 is a top plan view of an alternative embodiment of the disposable absorbent article with hidden lines to show interior construction and a corner folded back to show exterior construction.

FIG. 7 shows an embodiment illustrated as article 300 that may be partially or entirely flushable, compostable, and biodegradable, depending on the interior and exterior constructions. The backsheet 54 may be omitted, and a liquid permeable back liner 84 may be utilized as alternative material to backsheet 54. Back liner 84 is generally the garment-facing surface of article 300. Back liner 84 may be formed of the same material as top liner 52 and is preferably a substantially fluid permeable material that is flushable, biodegradable, and compostable. The top liner 52 and the back liner 84 may be joined to form a liquid permeable outer liner enclosure 90 (not shown) using bonding 64 materials and methods to form an envelope-like enclosure for the absorbent core 70. Optionally, back liner 84 may be omitted, and top liner 52 may be joined onto itself along its edges and attached using bonding 64 to form outer liner enclosure 90 (not shown) to enclose the absorbent core 70. Hidden lines show the outline of the absorbent core 70. Alternatively, the absorbent core 70 may be omitted; article 300 may include membrane 78 enveloping high-absorbency material 76. The various alternatives for the interior construction of article 300 are depicted in the cross-sectional views for FIGS. 2A to 2H.

Along the surface of top liner 52 may be incorporated ripping feature 56 to facilitate in detaching removable liner 58 from top liner 52. Ripping features 56 may comprise two parallel lines of relative weakness, or series of perforations, incorporated along length of the top liner 52. It is readily apparent that ripping features 56 may employ various configurations, shapes, sizes, or placements, and that ripping features 56 may also be incorporated along the back liner 84. Removable liner 58 and ripping features 56 are positioned within the area between leg seams 66. Sanitary grips 60 may be used in combination with gap 62. Sanitary grips 60 are the ends of removable liner 58 that may extend beyond the waist seams 68, and provide a sanitary placement to enable the user to quickly and easily grasp removable liner 58 proximate to one or both ends of article 300 to detach removable liner 58 from article 300. Detachment and disposal operations shown in FIGS. 3 to 6 for article 200 may also be employed for article 300 and performed over a toilet in preparation for disposal. Article 300 is shown having a rectangular shape; although, it is readily apparent that other shapes may also be utilized based upon design requirements.

FIG. 8 shows that the removable liner 58 may be completely detached from article 300 to create opening 80 along the surface of top liner 52, and to expose absorbent core 70. FIGS. 8A, 8B, and 8C are the cross-sectional views of article 300 in FIG. 8 comprising the interior constructions of FIGS. 5A, 5B, and 5C, respectively. Removable liner 58 is shown completely detached from article 300. After use, removable liner 58 may be partially or completely detached from article 300 and may be flushed in a toilet along with body exudates that may be contained on removable liner 58. It is readily apparent that removable liner 58 may also be composted or disposed in a landfill, and may be attached to or detached from article 300. The interior construction from FIG. 2J (not shown), comprising absorbent core 70 that combines absorbent material 74 and high-absorbency material 76, may be detached as shown in FIG. 8B, and after use, absorbent core 70 may remain attached to article remainder 86 and may be composted.

FIG. 9 shows that opening 80 may allow absorbent core 70 to be released from the interior of article 300. Article 300 may be inverted above a toilet to allow the absorbent core 70 to fall by gravity into a toilet to be flushed in a toilet, or composted. Although, absorbent core 70 is depicted as a whole unit, it may be in pieces after being released from article 300. Dispersal layer 72 may remain attached to article 300, or may be released after use. Hidden lines show outline of membrane 78 for FIGS. 9A and 9C.

Article remainder 86 comprises the shell of article 300 that remains after the removable liner 58 and absorbent core 70 have been removed from article 300. Article remainder 86 may comprise back liner 84 and the portion of top liner 52 that remains attached to back liner 84 after removable liner 58 has been removed, as well as any additional materials that may have been added to article 300, such as high-absorbency material 76 or membrane 78. After use, depending on the materials comprising article remainder 86, it may be flushed, composted, recycled or disposed in a landfill. Although high-absorbency material 76 may be expanded from the fluids that have been absorbed therein during use, once the fluids dry and evaporate the high-absorbency material 76 will shrink back substantially close to the original size, which will reduce the amount of material discarded.

FIG. 9A is the cross-sectional view of article 300 in FIG. 9 showing absorbent core 70 being released and may be flushed or composted after use. Article remainder 86 is shown having the interior construction of FIG. 8A and comprising high-absorbency material 76 enclosed between membrane 78 and back liner 84, which may be composted or disposed in a landfill.

FIG. 9B is the cross-sectional view of article 300 in FIG. 9 showing absorbent core 70 being released and may be flushed or composted after use. Article remainder 86 shows the interior construction of FIG. 8B comprising back liner 84, which may be flushed or composted.

FIG. 9C is the cross-sectional view of article 300 in FIG. 9 showing absorbent core 70 being released and may be flushed or composted after use. Article remainder 86 is shown having the interior construction of FIG. 8C and comprising high-absorbency material 76 enclosed between membrane 78 and back liner 84, which may be composted or disposed in a landfill.

Figure 10:
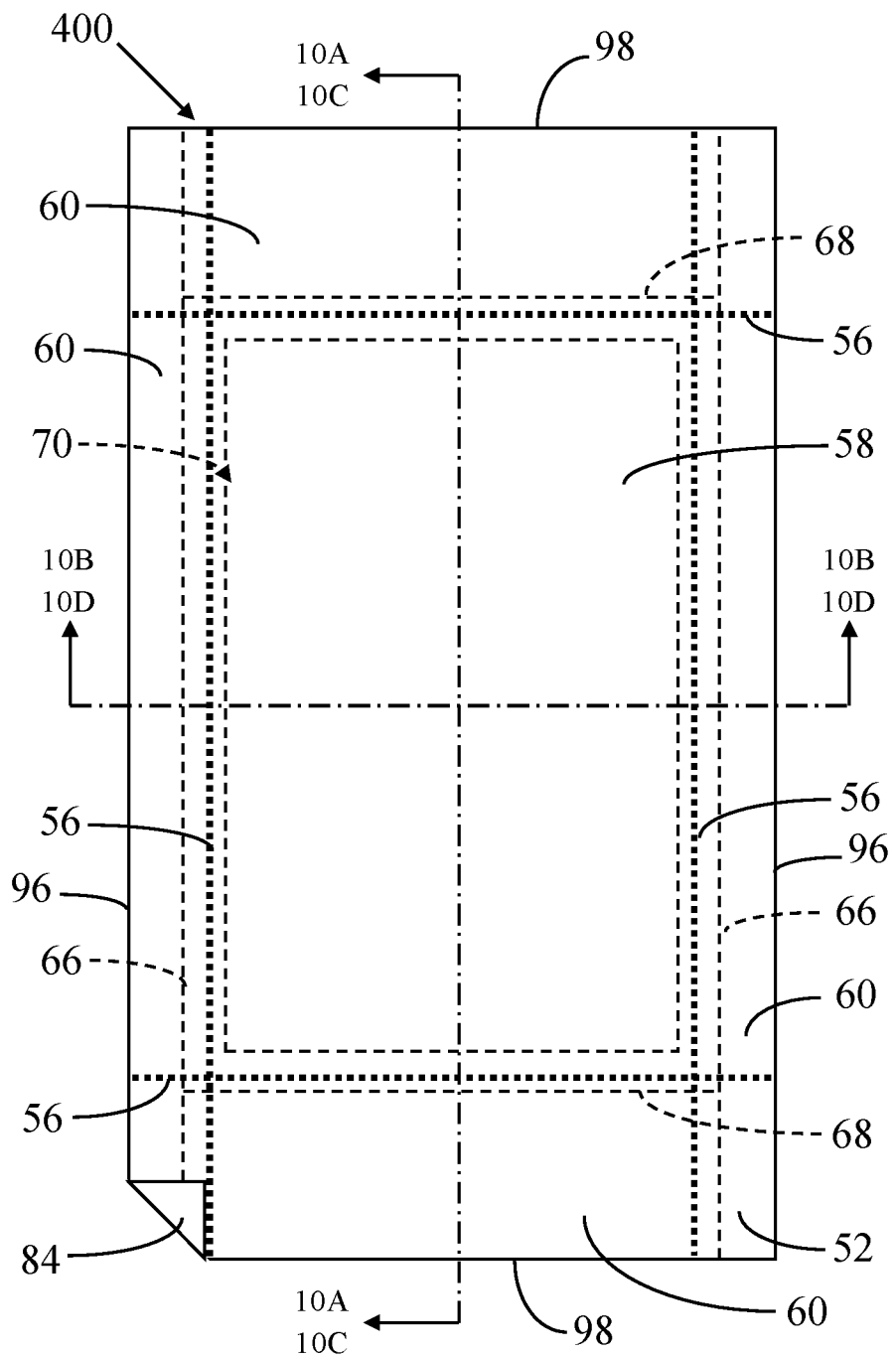
FIG. 10 is a top plan view of another embodiment of the disposable absorbent article with hidden lines to show interior construction and having a corner folded back to show exterior construction.

FIG. 10 depicts an embodiment illustrated as article 400 that may be entirely flushable, compostable, and biodegradable. Back liner 84 may be formed of the same material as the top liner 52 and is preferably a substantially fluid permeable material that is flushable, compostable, and biodegradable. Ripping feature 56 may be formed symmetrically along surfaces of both top liner 52 and back liner 84; accordingly, top liner 52 and back liner 84 may be identical, and may be oriented interchangeably during use. Top liner 52 and the back liner 84 may be joined to form a liquid permeable outer liner 90 using bonding 64 methods to form an envelope-like enclosure for absorbent core 70. Optionally, back liner 84 may be omitted, and top liner 52 may be joined onto itself along its edges and attached using bonding 64 to form outer liner enclosure 90 (not shown) and enclose the absorbent core 70. Hidden lines show the outline of absorbent core 70. Article 400 is shown having a rectangular shape; although, it is readily apparent that other shapes may also be utilized based upon design requirements.

The ripping feature 56 comprises a grid of two sets of parallel lines of relative weakness, or series of perforations that may be incorporated along top liner 52 and back liner 84 throughout the length and width of article 400, and may be placed slightly inward of waist seams 68 and leg seams 66, as depicted in FIG. 10; although other configurations may also be used. This simple grid configuration for the ripping feature 56 may allow the manufacturer the option to utilize a material that is pre-perforated for top liner 52 and back liner 84 prior to the assembly process of article 400, rather than during, which may minimize the modifications and cost requirements for retrofitting existing equipment and processes necessary to apply ripping features 56 to the top liner 52 during the assembly process of article 400.

Sanitary grips 60 may be formed by integral extensions of article 400 that may extend beyond waist seams 68. Sanitary grips 60 may be used in combination with gap 62. Sanitary grips 60 may also extend beyond the leg seams 66. As a result of the distance of the exudation points, sanitary grips 60 are less likely to be soiled at the time replacement of article 400 becomes necessary or desirable. Sanitary grips 60 may provide a sanitary placement for the user to grasp and detach article 400 with the optimum level of ease and convenience to the user.

FIGS. 10A to 10D depict cross-sectional views showing various alternatives for the interior construction of the embodiment of article 400, shown in FIG. 10. Top liner 52 and back liner 84 are shown forming an envelope-like enclosure for absorbent core 70 comprising absorbent material 74 and dispersal layers 72. Absorbent material 74 is shown disposed between two dispersal layers 72. Dispersal layer 72 may be omitted entirely. The surfaces of top liner 52 and back liner 84 may incorporate ripping feature 56. The ripping feature 56 may be incorporated along top liner 52 and back liner 84, and may be placed slightly inward of waist seams 68 and leg seams 66, as depicted in FIG. 10. The configurations and placements for ripping feature 56 may be symmetrical along the top liner 52 and back liner 84. It is readily apparent that the ripping feature 56 may employ various configurations, shapes, sizes, placements, or may be omitted entirely, based upon the design requirements.

Figure 10A:
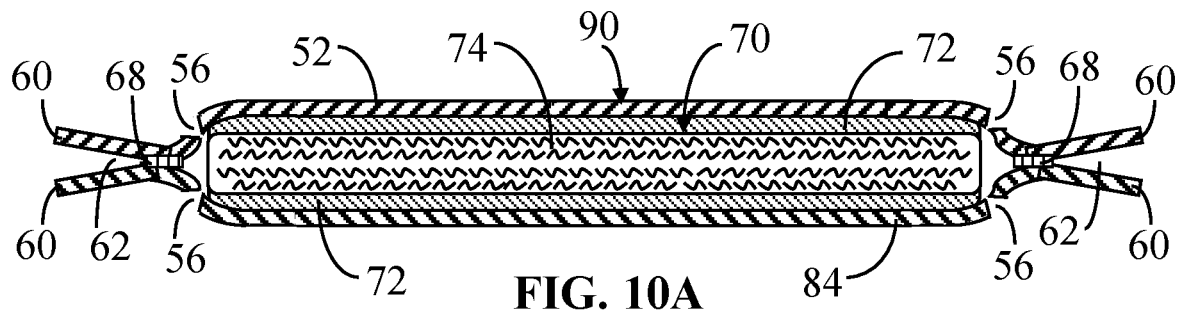
FIG. 10A is a cross-sectional view taken along line 10A-10A of FIG. 10.
Figure 10B:
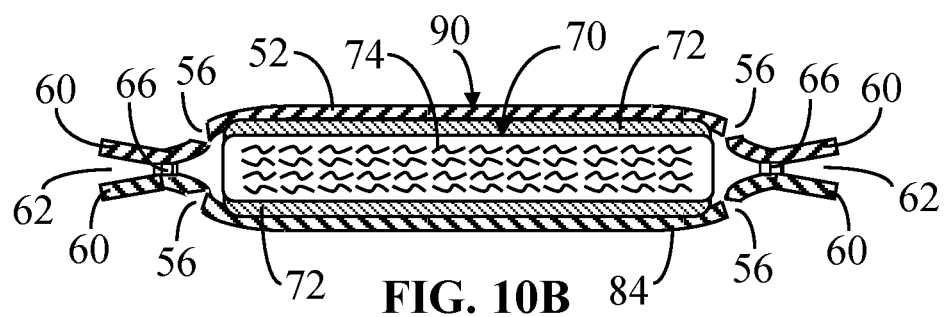
FIG. 10B is a cross-sectional view taken along line 10B-10B of FIG. 10.
Figure 10C:
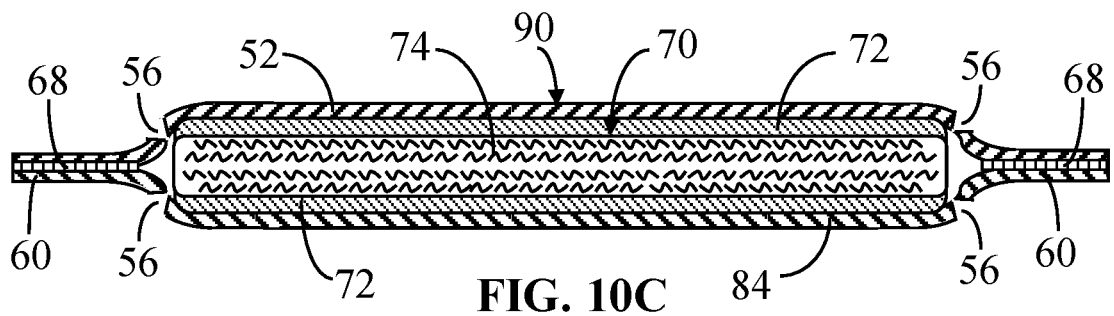
FIG. 10C is a cross-sectional view taken along line 10C-10C of FIG. 10.
Figure 10D:
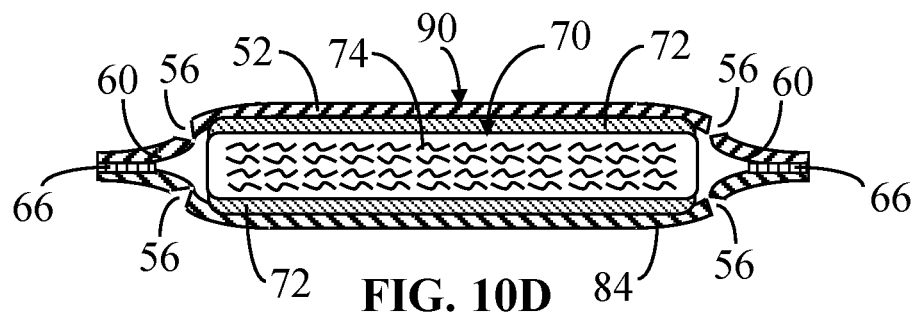
FIG. 10D is a cross-sectional view taken along line 10D-10D of FIG. 10.

Article 400 may be manufactured to comprise various combinations of configurations that may include the combinations of FIGS. 10A and 10B, or of FIGS. 10C and 10D. Alternatively, article 400 may also comprise the combinations of FIGS. 10A and 10D, or of FIGS. 10B and 10C.

FIGS. 10A and 10B show the cross-sectional views along the centerlines of the length and width of article 400, respectively. Sanitary grips 60 may be unattached to form the opened space of the gap 62 extending beyond the outer edges of the leg seams 66 and waist seams 68. This configuration of sanitary grips 60 provides a sanitary placement to enable the user to quickly and easily grasp the removable liner 58 proximate one or both ends of article 400 along sanitary grips 60 that extend beyond the waist seams 68 to detach removable liner 58 from the article 400, as shown for articles 200 and 300. Alternatively, the user may grasp sanitary grips 60 along any of the outer edges that extend beyond leg seams 66 or waist seams 68 to pull sanitary grips 60 outward from gap 62 to separate top liner 52 and back liner 84 and create an opening 80 to release absorbent core 70.

FIGS. 10C and 10D show the cross-sectional views along the centerlines of the length and width of article 400, respectively. Sanitary grips 60 may be attached to omit gap 62 and may extend outward beyond ripping features 56 shown along the leg seams 66 and waist seams 68. This configuration of sanitary grips 60 enables the user to grasp any of the sanitary grips 60 that extend beyond the leg seams 66 or waist seams 68 to tear open article 400 by detaching the sanitary grips 60 along ripping features 56.

Figure 11:
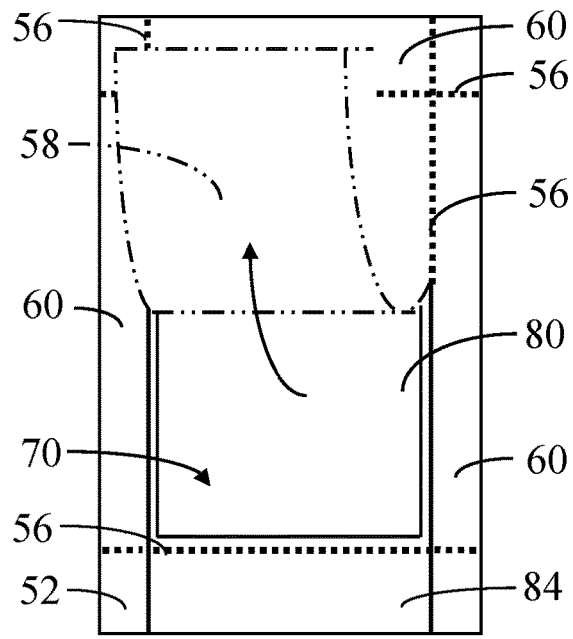
FIG. 11 is a perspective view of a detachment option of disposable absorbent article of FIG. 10.
Figure 12:
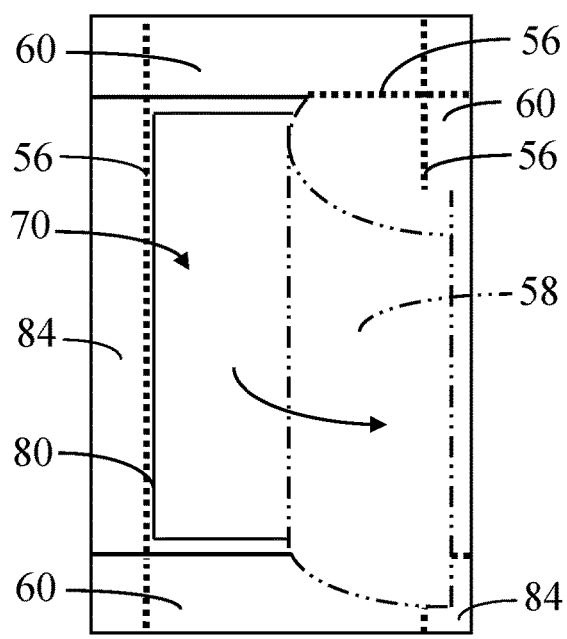
FIG. 12 is a perspective view of a detachment option of disposable absorbent article of FIG. 10.

FIGS. 11 and 12 show examples for the detachment operation of article 400 after use that may be performed above a toilet. Removable liner 58 may be detached from article 400 using the ripping features 56 that are adjacent to leg seams 66 or waist seams 68, shown in FIGS. 11 and 12, respectively. After removable liner 58 has been detached, opening 80 is created, which allows absorbent core 70 to be released from article 400 to be composted or flushed in a toilet. After use, removable liner 58 may be partially detached or completely removed from article 400 to be flushed along with body exudates contained on it, and article remainder 86 may be flushed or composted.

Figure 13:
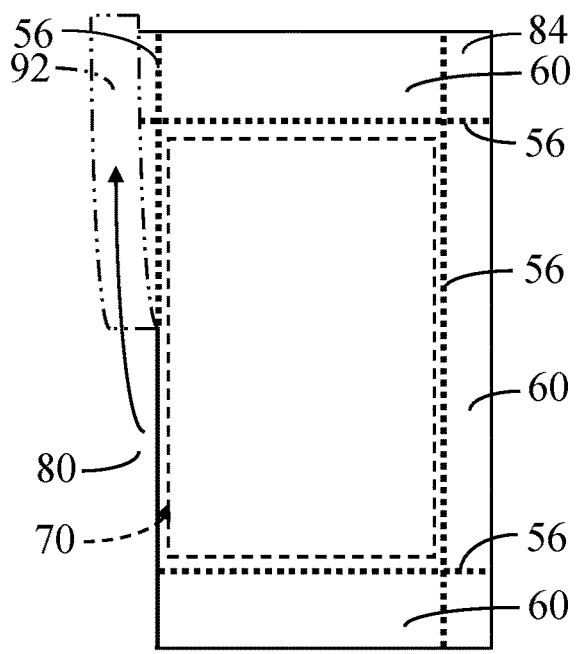
FIG. 13 is a perspective view of a detachment option of disposable absorbent article of FIG. 10.
Figure 14:
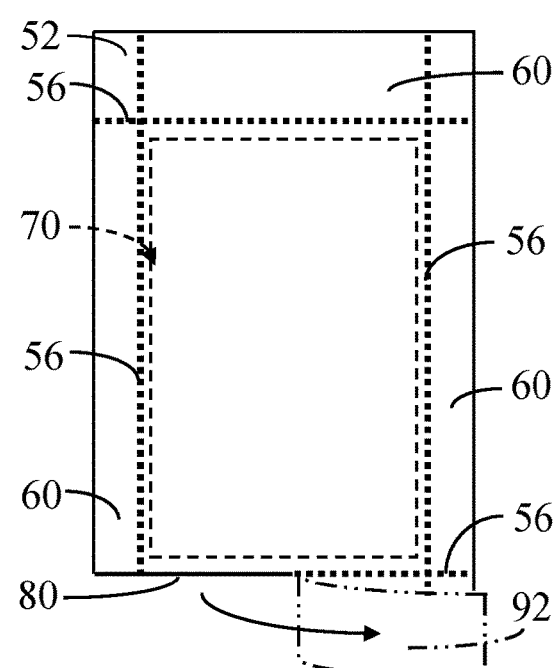
FIG. 14 is a perspective view of a detachment option of disposable absorbent article of FIG. 10.

FIGS. 13 and 14 show alternative examples for the detachment operation of article 400 after use that may be performed above a toilet. Sanitary grips 60 provide a sanitary placement for handling and opening article 400, and allow the user to be better enabled to avoid contacting the wearer's exudates with the user's hands when separating sanitary grip 60 from article 400. The user may grasp one or more of the sanitary grips 60 to detach from article 400 by tearing along ripping feature 56 adjacent to leg seams 66 or waist seams 68, shown in FIGS. 13 and 14, respectively. Detached grip 92 is shown partially detached from article 400.

Detached grip 92 is the portion of the sanitary grip 60, comprising top liner 52 and back liner 84, or outer liner 90, which is partially or entirely detached from article 400 to create opening 80. Detached grip 92 may be flushed or composted after use.

Figures 15, 15A:
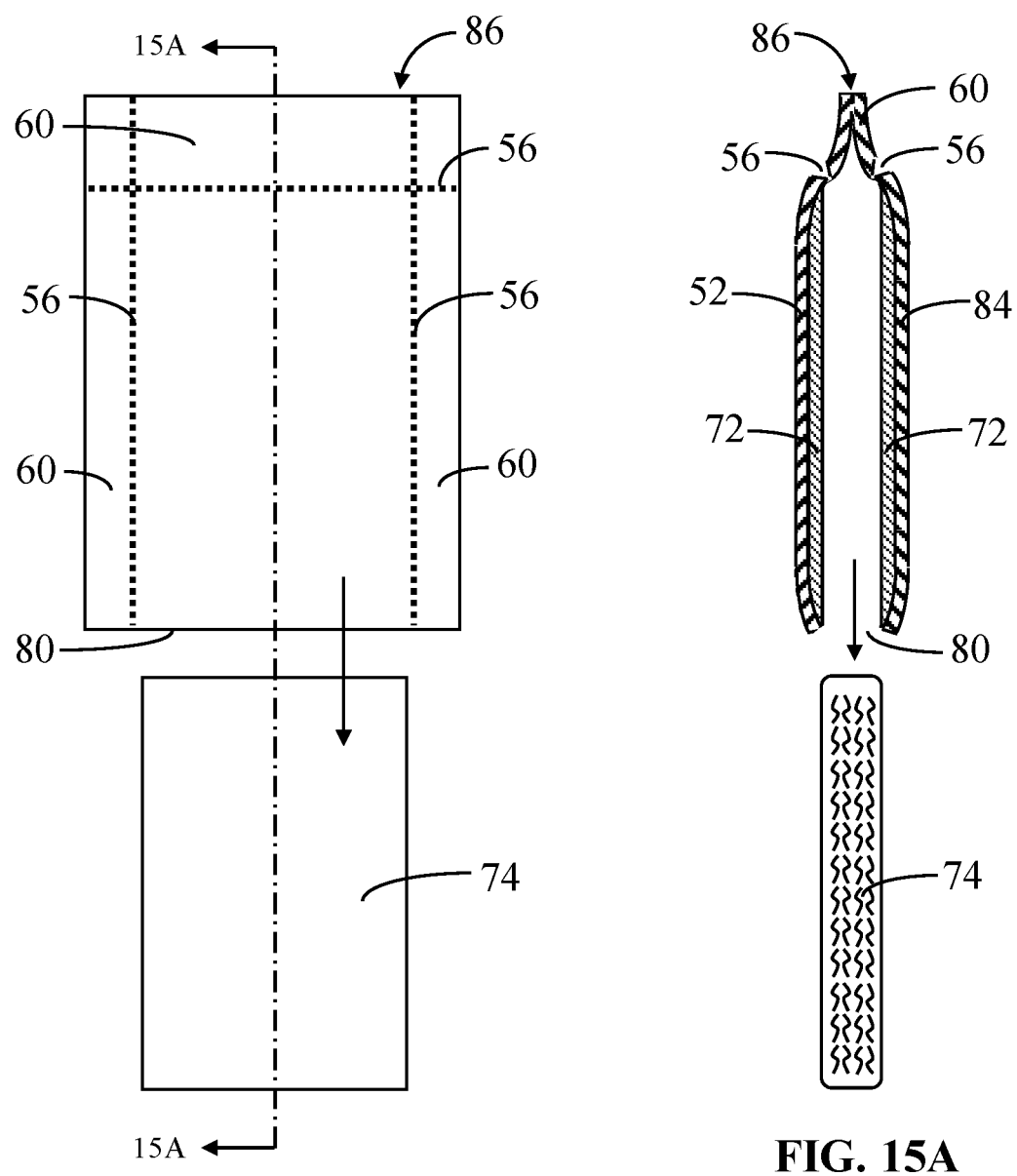
FIG. 15 is a perspective view of a step in the disposal of disposable absorbent article of FIG. 10.
FIG. 15A is a cross-sectional view taken along line 15A-15A of FIG. 15.

FIG. 15 shows a subsequent step in the detachment operation of FIGS. 13 and 14 of article 400 after detached grip 92 has been completely removed from article 400. The absorbent core 70 is shown being released through opening 80 from article remainder 86. Article 400 may be held above a toilet to allow the absorbent core 70 to fall by gravity into a toilet to be flushed, or may be composted. The article remainder 86 comprises the shell of article 400 that remains after absorbent core 70 has been removed, and may be flushed or composted after use.

FIG. 15A is the cross-sectional view of FIG. 15 showing the interior construction of article remainder 86, and showing absorbent core 70 being released through opening 80. Absorbent core 70 may be flushed or composted after use. Article remainder 86 comprises the portions of top liner 52, back liner 84, and dispersal layer 72 that remain attached to article 400 after absorbent core 70 has been removed from article 400. The article remainder 86 may be flushed or composted after use.

FIGS. 16 to 27 depict alternative embodiments for articles 100 to 400 that may be partially or entirely flushable, compostable, and biodegradable, depending on the interior or exterior constructions. Various shapes, placements, and configuration for ripping feature 56 may be utilized; although, it is readily apparent that other shapes, placements, and configurations may also be used. After use, absorbent core 70 may be released and composted, or flushed in a toilet. Removable liner 58 may be entirely detached and flushed along with body exudates contained on it, or may be partially attached and may be disposed with article remainder 86. After use, article remainder 86 and detached grip 92 may be flushed, composted, recycled, or disposed in a landfill, as described for the disposal of articles 100 to 400.

Figure 16:
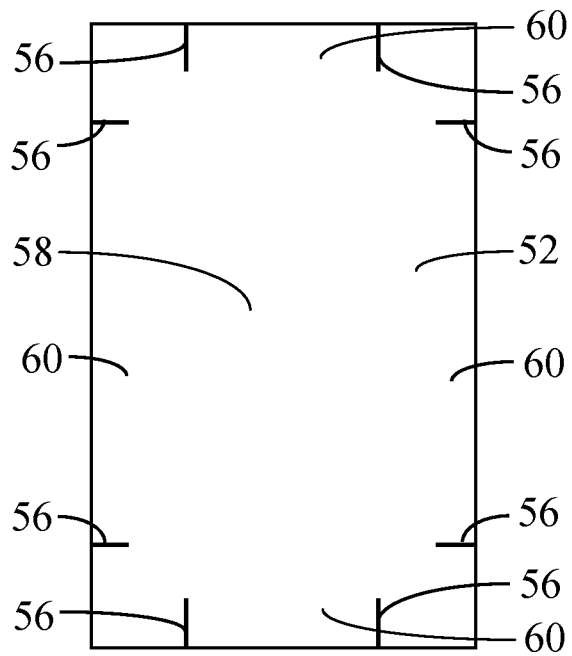
FIGS. 16 to 23 show plan views of alternative embodiments of the disposable absorbent articles of FIGS. 1, 2, 7, and 10.

FIG. 16 depicts another embodiment that may be entirely flushable, compostable, and biodegradable. The ripping feature 56 may comprise one or more slits, or cuts positioned along the edges of top liner 52 and back liner 84, or outer liner 90, extending outward beyond waist seams 68 and leg seams 66. Ripping features 56 may be aligned inward of waist seams 68 and leg seams 66. After use, the user may release absorbent core 70 by detaching removable liner 58 or by grasping any of the ripping features 56 to tear open article 400.

Figure 17:
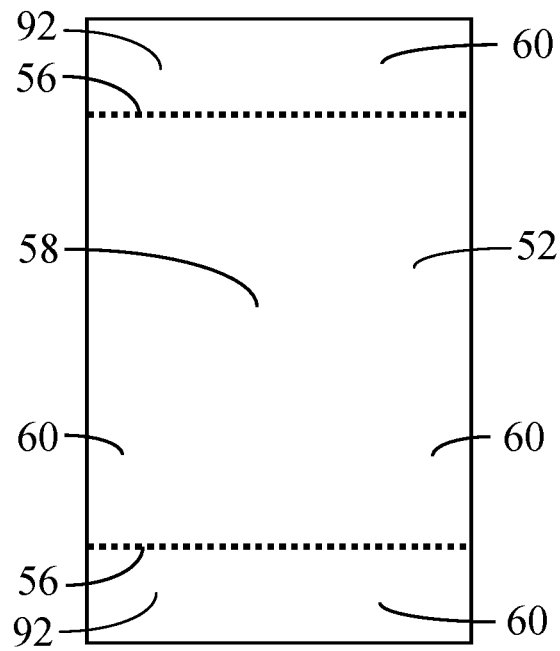

FIG. 17 depicts an alternative embodiment that may be entirely flushable, compostable, and biodegradable. Ripping feature 56 may comprise two parallel lines of relative weakness, or series of perforations that may be incorporated along the entire widths of the top liner 52 and back liner 84, positioned inward waist seams 68, and optionally, one line of ripping feature 56 may be used instead of two. It is readily apparent that variations in the position and orientation of ripping feature 56 maybe be utilized. After use, the user may detach removable liner 58, as described in FIG. 12, and release absorbent core 70. Alternatively, the user may grasp either sanitary grip 60 to tear and remove detached grip 92 along ripping feature 56, as described in FIGS. 14 and 15, and release absorbent core 70.

Figure 18:
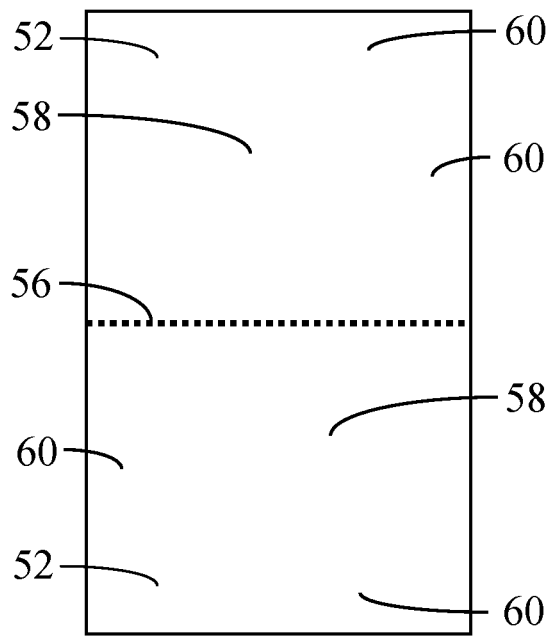

FIG. 18 depicts another embodiment that may be entirely flushable, compostable, and biodegradable. Ripping feature 56 may comprise one line of relative weakness, or series of perforations that may be incorporated along the center of top liner 52 and of back liner 84. It is readily apparent that variations in the position and orientation of ripping feature 56 maybe be utilized. The user may grasp either sanitary grip 60 located above or below ripping feature 56 to detach either removable liner 58, as described in FIG. 12, and release absorbent core 70 after use. Alternatively, the user may grasp either sanitary grip 60 to detach top liner 52 and back liner 84 along ripping feature 56 and release absorbent core 70, as described in FIGS. 14 and 15.

Figure 19:
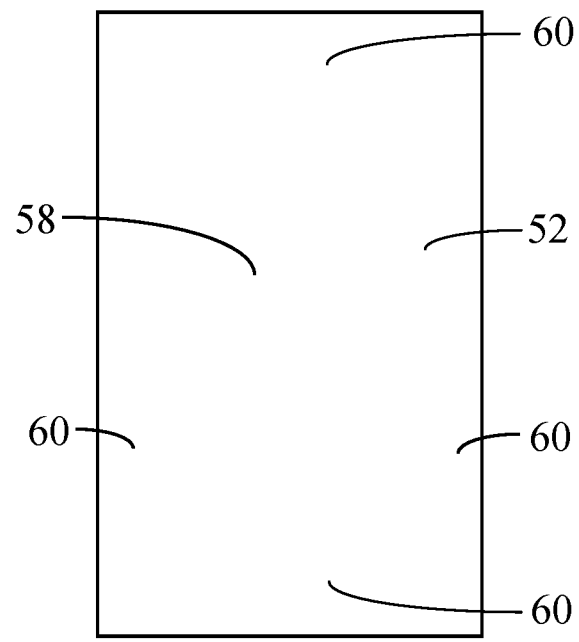

FIG. 19 depicts an alternative embodiment that does not utilize ripping features 56. One or more sanitary grips 60 may be used. After use, the user may grasp and pull on either sanitary grip 60 to tear along and detach removable liner 58 and release absorbent core 70 to flush in a toilet or compost. Alternatively, the user may grasp sanitary grips 60 along any of the edges that extend beyond leg seams 66 or waist seams 68 to pull sanitary grips 60 outward from gap 62 to create opening 80 and to release the absorbent core 70. Removable liner 58 may be partially detached or completely detached to be flushed along with body exudates contained on it.

Figure 20:
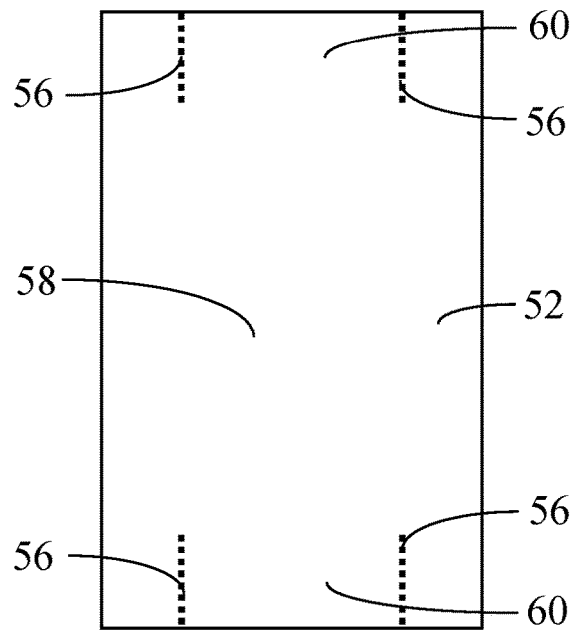

FIG. 20 depicts ripping features 56 that may comprise one or more lines of relative weakness, or series of perforations along one or more of the sanitary grips 60, and may be positioned to be aligned inward from the leg seams 66. After use, the user may pull on either sanitary grip 60 along ripping feature 56 and may detach the removable liner 58 to release the absorbent core 70. Alternatively, the user may grasp either sanitary grip 60 to detach top liner 52 and back liner 84 along ripping feature 56, as described in FIGS. 13 and 15 to release absorbent core 70 after use.

Figure 21:
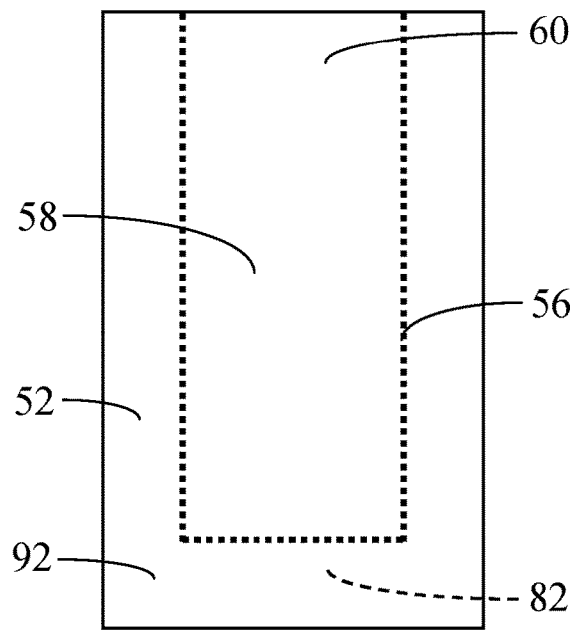

FIG. 21 depicts an alternative embodiment that may utilize a U-shaped configuration for ripping feature 56. Ripping feature 56 comprises two parallel lines of relative weakness, or series of perforations, which may be located parallel to and inward from the leg seams 66, and one line of relative weakness, or series of perforations placed parallel to and inward from waist seam 68 that is adjacent to waist feature 82. It is readily apparent that sanitary grip 60 may be used as an alternative to waist feature 82. After use, the user may pull on sanitary grip 60 along ripping feature 56 to detach removable liner 58 to release absorbent core 70. Alternatively, if sanitary grip 60 is used in place of waist feature 82, the user may tear detached grip 92 along ripping feature 56 to release absorbent core 70, and may flush or compost detached grip 92.

Figure 22:
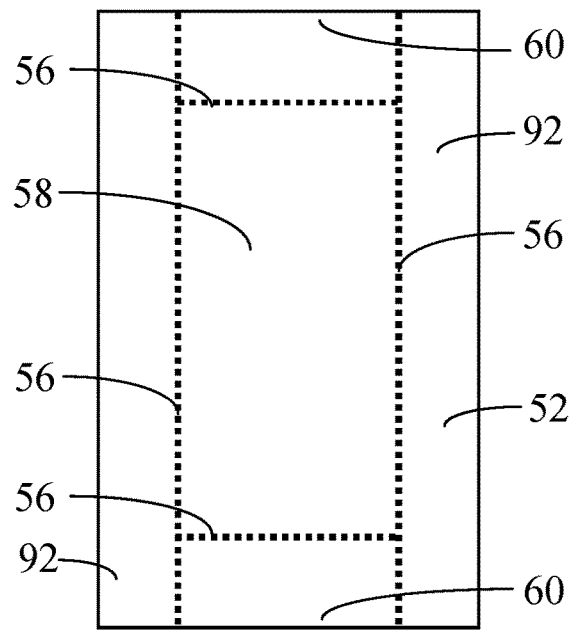
Figure 26:
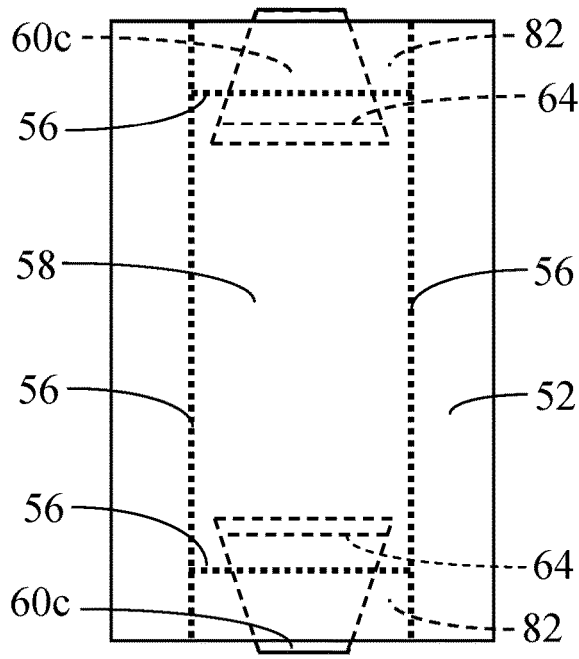
FIG. 26 is a plan view of disposable absorbent article from FIG. 22 with additional component.

FIG. 22 depicts ripping features 56 that may comprise two parallel lines of relative weakness, or series of perforations that may be located parallel to and inward from leg seams 66, throughout the length of the article of FIG. 22. Ripping feature 56 may comprise two additional parallel lines of relative weakness, or series of perforations that may be located parallel to and inward from waist seams 68, and may be placed between leg seams 66; it is readily apparent that ripping feature 56 may extend the width of the article of FIG. 22, or may be omitted. After use, the user may pull on sanitary grip 60 to tear along ripping feature 56 to detach removable liner 58 and release absorbent core 70. Alternatively, the user may tear detached grip 92 along ripping feature 56 to release absorbent core 70, and may flush or compost detached grip 92. Waist features 82 may be used as alternatives to sanitary grips 60 as shown in FIG. 26.

Figure 23:
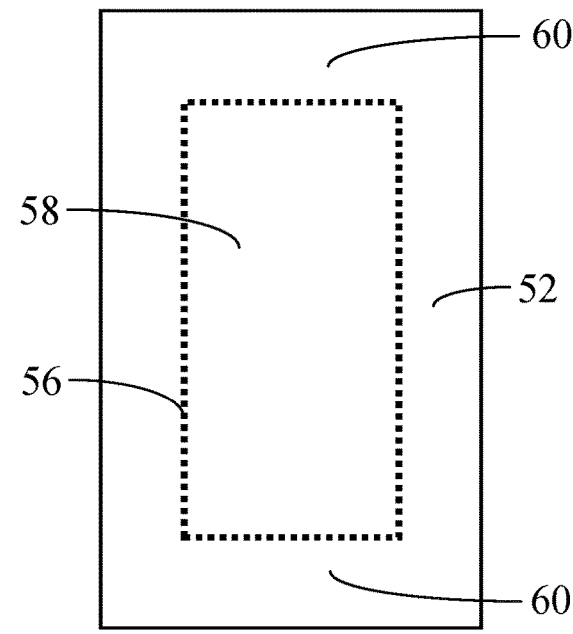
Figure 27:
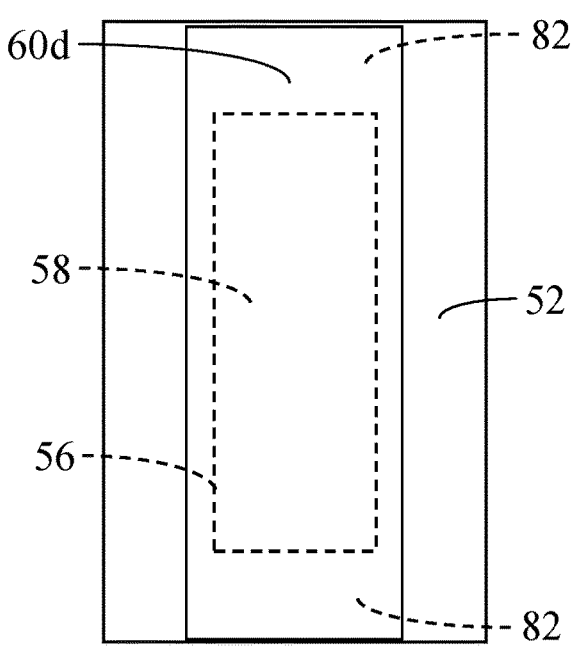
FIG. 27 is a plan view of disposable absorbent article from FIG. 23 with additional component.

FIG. 23 depicts a ripping feature 56 may comprise a rectangular shape and placed inward from leg seams 66 and waist seams 68; although, it is readily apparent that the ripping feature 56 may employ other shapes. After use, the user may pull on sanitary grip 60 along ripping feature 56 to detach removable liner 58 and release absorbent core 70. Waist features 82 may be used as an alternative to sanitary grips 60 as shown in FIG. 27.

Figure 24:
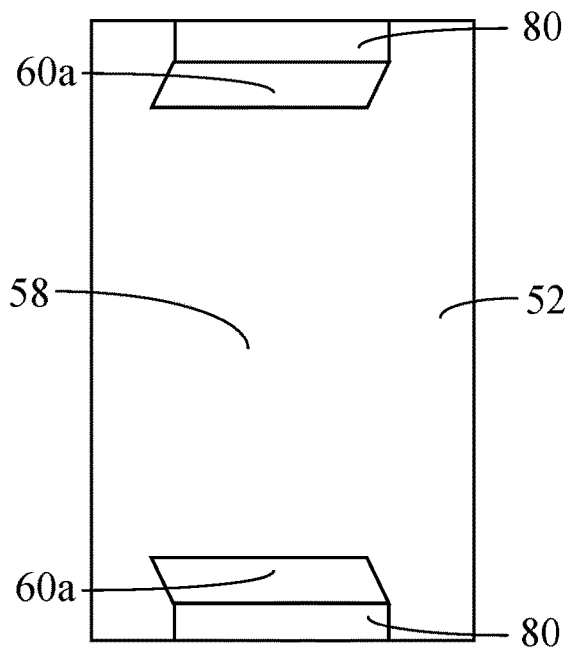
FIG. 24 is a perspective view of another embodiment of disposable absorbent article of FIG. 19.

FIG. 24 depicts an alternative embodiment of article from FIG. 19 showing two sanitary grips 60a that may comprise integral sections of top liner 52, or outer liner 90, that have been cut inward of leg seams 66 to create an opening 80 along top liner 52, and that may be folded to overlap the top liner 52; it is readily apparent that sanitary grips 60a may remain unfolded. Sanitary grips 60a may be used in combination with gap 62, or gap 62 may be omitted. Sanitary grip 60a may provide a visual guide for the user to identify how to initiate detaching removable liner 58. The user may pull on one or both sanitary grips 60a to detach removable liner 58 and release absorbent core 70. One or two sanitary grips 60a from FIG. 24 may be used in combination with articles 100 to 400 or embodiments shown in FIGS. 16 to 23, to facilitate in detaching removable liner 58.

Figure 25:
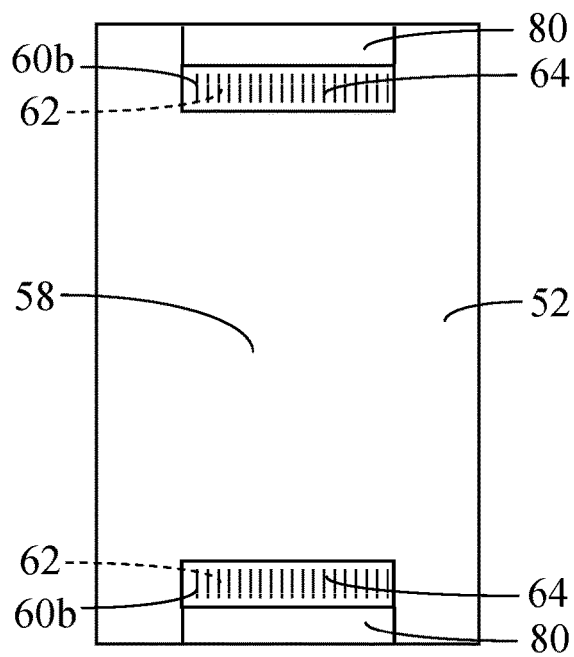
FIG. 25 is a perspective view of another embodiment of disposable absorbent article of FIG. 19.

FIG. 25 depicts an alternative embodiment of article from FIG. 19 showing two sanitary grips 60b that may comprise integral sections of top liner 52 that have been cut inward of leg seams 66 to create an opening 80 along top liner 52, and that may be folded over and attached to top liner 52 using bonding 64 methods and materials. Sanitary grips 60b may be used in combination with the sanitary gap 62, or gap 62 may be omitted. Sanitary grip 60b may provide a visual guide for user in detaching removable liner 58. The user may pull on one or both sanitary grips 60b to detach removable liner 58 and release absorbent core 70. One or two sanitary grips 60b from FIG. 25 may be used in combination with articles 100 to 400 or embodiments shown in FIGS. 16 to 24, to facilitate in detaching removable liner 58.

FIG. 26 depicts an alternative embodiment that may have two supplementary sanitary grips 60c that may be superimposed and attached to the article from FIG. 22, shown having a trapezoid shape; although, it is readily apparent that other shapes, sizes, placements, and configurations may also be utilized. Sanitary grip 60c may be attached to the removable liner 58, top liner 52, or sanitary grip 60, using bonding 64 methods and materials. Sanitary grip 60c may be formed of the same material as the top liner 52, which is preferably a substantially fluid permeable material that is flushable, biodegradable, and compostable. Sanitary grip 60c may be used in combination with the sanitary gap 62, or gap 62 may be omitted; alternatively, sanitary grip 60c may be utilized in combination with articles employing waist features 82. After use, the user may pull on one or both sanitary grips 60c to detach removable liner 58 and release absorbent core 70. Sanitary grip 60c may be flushed along with removable liner 58. Optionally, one or more sanitary grips 60c may be used in combination with articles 100 to 400 or embodiments shown in FIGS. 16 to 25, for reinforcement in detaching removable liner 58.

FIG. 27 depicts an alternative embodiment showing a supplementary sanitary grip 60d that may overlay article from FIG. 23 and may be attached to removable liner 58, top liner 52, or sanitary grip 60 using bonding 64; optionally, sanitary grip 60d may be used in combination with embodiments shown in FIGS. 16 to 25 or articles 100 to 400. Sanitary grip 60d may provide reinforcement to detach removable liner 58. Sanitary grip 60d may allow the user to be better enabled to avoid contacting the wearer's exudates with the user's hands when detaching removable liner 58. Sanitary grip 60d may be formed of the same material as top liner 52 that may be a substantially fluid permeable material that is flushable, biodegradable, and compostable. Sanitary grip 60d is shown extending throughout the length of the article and having a rectangular shape; although, it is readily apparent that other shapes, sizes, placements, and configurations may also be used. Sanitary grip 60d may be utilized in combination with articles employing waist features 82 to facilitate in detaching removable liner 58 from top liner 52. Sanitary grip 60d may also be used in combination with the sanitary gap 62, or gap 62 may be omitted. Ripping features 56 may also be incorporated along sanitary grip 60d. Optionally, opening 80 may replace removable liner 58 and sanitary grip 60d may enclose opening 80. After use, the user may pull on sanitary grip 60d to release absorbent core 70. Sanitary grip 60d may be flushed after use.

CONCLUSIONS AND RAMIFICATIONS

The detailed description of this disclosure has been made in the context of a disposable diaper article. It is readily apparent, that the absorbent structure of the present disclosure would also be suitable for other absorbent articles, such as, disposable inserts, disposable absorbent pads, disposable training pants, disposable incontinence articles, feminine care pads, and the like.

The foregoing detailed description has been for the purpose of illustration. In the description, reference is made to the accompanying drawings which illustrate some embodiments of the disclosure. Variations in the operation and utilization of the disclosure are applicable. Also, alternative absorbent materials may be substituted for those described herein. Further, many of the particular aspects, features, or disposal options described in relation to one embodiment may be implemented in combination with aspects of other embodiments.

While particular embodiments of the present disclosure have been illustrated and described, these should not be construed as limiting the scope of the embodiments, but as merely providing illustrations of some embodiments. It would be obvious to those skilled in the art that the disclosure is capable of other and different embodiments, and that various other changes and modifications may be made without departing from the spirit and scope of the present disclosure. Accordingly, the scope of the disclosure should be determined not by the embodiments illustrated, but by the appended claims and their legal equivalents.

I claim:

1. A detachable disposable absorbent article, comprising:
   a. a wearer-facing continuous first liner that is liquid permeable;
   b. a garment-facing second liner that is substantially liquid permeable and directly bonded to the first liner by one or more seams, one or more seams shifted inward from the article edge form a sanitary gap between the second liner and a sanitary grip, said sanitary grip is a continuous extension of the first liner that is unattached to the second liner outward of the seam at the article edge; and
   c. a liquid permeable absorbent core enclosed between the first liner and the second liner; whereby said sanitary grip is adapted to provide a sanitary placement for tearing the first liner to break an opening that is adapted to release the absorbent core.

2. The article of claim 1, wherein a breakable bond forms at least one of the seams.

3. The article of claim 1, wherein the first liner is adapted to be torn to form a removable liner that is continuous to the first liner.

4. The article of claim 1, wherein the first liner is adapted to be flushed.

5. The article of claim 1, wherein the first liner is adapted to be composted.

6. The article of claim 1, wherein the absorbent core is adapted to be flushed.

7. The article of claim 1, wherein the absorbent core is adapted to be composted.

8. The article of claim 1, wherein the first liner having a ripping feature formed therein, wherein the ripping feature is adapted for tearing the first liner.

9. The article of claim 8, wherein the second liner having a ripping feature formed therein and placed in alignment with the ripping feature of the first liner, wherein the ripping features are adapted for tearing the first liner and the second liner.

10. The article of claim 1, wherein the second liner is adapted to be torn to form a removable liner that is continuous to the second liner.

11. The article of claim 1, wherein the second liner is adapted to be flushed.

12. The article of claim 1, wherein the second liner is adapted to be composted.

13. The article of claim 1, wherein the second liner is adapted to be recycled.

14. The article of claim 1, wherein the absorbent core comprises a high-absorbency material and a liquid permeable membrane adapted to form a barrier for said high-absorbency material, and wherein the membrane is adapted to prevent said high-absorbency material from escaping and from being flushed after tearing open the article.

15. The article of claim 14, wherein said high-absorbency material is adapted to be composted.

16. The article of claim 14, wherein the membrane is adapted to be composted.

17. The article of claim 1, further comprising at least one fastener section attached to the article.

18. The article of claim 1, further comprising at least one attachment component adapted to secure the article for use.

19. The article of claim 1, further comprising at least one supplementary sanitary grip adapted to provide reinforcement for tearing open the first liner, wherein at least one of the supplementary sanitary grips is adapted to be flushed or composted.

20. The article of claim 1, wherein a removable portion of the first liner and a removable portion of the second liner are adapted to be torn from the article to form a detached grip.

* * * * *